(12) United States Patent
Jaquish et al.

(10) Patent No.: US 11,826,611 B2
(45) Date of Patent: *Nov. 28, 2023

(54) DEVICES FOR EXERCISE APPARATUSES

(71) Applicant: Jaquish Biomedical Corporation, Nevada City, CA (US)

(72) Inventors: Paul Edward Jaquish, Nevada City, CA (US); John Paul Jaquish, Nevada City, CA (US); Henry David Alkire, Nevada City, CA (US)

(73) Assignee: Jaquish Biomedical Corporation, Nevada City, CA (US)

( * ) Notice: Subject to any disclaimer, the term of this patent is extended or adjusted under 35 U.S.C. 154(b) by 530 days.

This patent is subject to a terminal disclaimer.

(21) Appl. No.: 16/862,822

(22) Filed: Apr. 30, 2020

(65) Prior Publication Data

US 2020/0254294 A1 Aug. 13, 2020

Related U.S. Application Data

(63) Continuation of application No. 15/758,291, filed as application No. PCT/US2016/052302 on Sep. 16, (Continued)

(51) Int. Cl.
*A63B 23/035* (2006.01)
*A63B 21/00* (2006.01)
(Continued)

(52) U.S. Cl.
CPC .... *A63B 23/03525* (2013.01); *A63B 21/0058* (2013.01); *A63B 21/00069* (2013.01);
(Continued)

(58) Field of Classification Search
CPC ........ A63B 23/03525; A63B 21/00069; A63B 21/00072; A63B 21/0058; A63B 21/0087;
(Continued)

(56) References Cited

U.S. PATENT DOCUMENTS 4,466,610 A 8/1984 Israel
4,556,214 A 12/1985 Petrofsky et al.
(Continued)

FOREIGN PATENT DOCUMENTS

EP 1166826 1/2002
JP 2009-225845 A 10/2009
(Continued)

OTHER PUBLICATIONS

Jaquish J., "Multiple-of-bodyweight axial bone loading using novel exercise intervention with and without bisphosphonate use for osteogenic adaptation", Osteoporosis International, vol. 198, Supplement 24, Dec. 4, 2013, pp. S594-S595.
(Continued)

*Primary Examiner* — Sundhara M Ganesan
(74) *Attorney, Agent, or Firm* — MORGAN, LEWIS & BOCKIUS LLP

(57) ABSTRACT

A device for an exercise apparatus includes a linear adjustment system and a sensor coupled to the linear adjustment system. The exercise apparatus includes a loading interface and a frame coupled to the loading interface for performing an exercise. The linear adjustment system fixes the loading interface of the exercise apparatus at any one of a plurality of functional positions in a functional range of the loading interface. The sensor measures the force exerted on the linear adjustment system. A correlating mechanism is used to correlate the force exerted on the linear adjustment system with the force exerted on the loading interface. The device allows exercisers to exert high or maximum loads in any one of a plurality of positions throughout their entire range of motion without first passing through a weak range of motion.

20 Claims, 25 Drawing Sheets

Related U.S. Application Data 2016, now Pat. No. 10,675,497, which is a continuation of application No. 14/859,085, filed on Sep. 18, 2015, now abandoned.

(60) Provisional application No. 62/329,999, filed on Apr. 29, 2016.

(51) Int. Cl.

| | | |
|---|---|---|
| *A63B 23/04* | (2006.01) | |
| *A63B 21/005* | (2006.01) | |
| *A63B 23/02* | (2006.01) | |
| *A63B 24/00* | (2006.01) | |
| *A63B 71/06* | (2006.01) | |
| *A63B 23/12* | (2006.01) | |
| *A63B 21/078* | (2006.01) | |
| *A63B 21/062* | (2006.01) | |
| *A63B 23/00* | (2006.01) | |
| *A63B 21/008* | (2006.01) | |
| *G16H 20/30* | (2018.01) | |
| *G16H 50/30* | (2018.01) | |
| *G16H 40/63* | (2018.01) | |
| *A63B 5/22* | (2006.01) | |

(52) U.S. Cl.
CPC .... *A63B 21/00072* (2013.01); *A63B 21/0087* (2013.01); *A63B 21/4034* (2015.10); *A63B 21/4047* (2015.10); *A63B 23/0216* (2013.01); *A63B 23/0405* (2013.01); *A63B 23/0429* (2013.01); *A63B 24/0062* (2013.01); *G16H 20/30* (2018.01); *G16H 40/63* (2018.01); *G16H 50/30* (2018.01); *A63B 5/22* (2013.01); *A63B 21/00* (2013.01); *A63B 21/00181* (2013.01); *A63B 21/0628* (2015.10); *A63B 21/078* (2013.01); *A63B 21/151* (2013.01); *A63B 21/159* (2013.01); *A63B 21/4011* (2015.10); *A63B 21/4035* (2015.10); *A63B 23/0211* (2013.01); *A63B 23/03508* (2013.01); *A63B 23/1209* (2013.01); *A63B 23/1263* (2013.01); *A63B 23/1281* (2013.01); *A63B 24/0003* (2013.01); *A63B 24/0087* (2013.01); *A63B 71/0622* (2013.01); *A63B 2023/003* (2013.01); *A63B 2024/0093* (2013.01); *A63B 2071/0658* (2013.01); *A63B 2208/0204* (2013.01); *A63B 2208/0214* (2013.01); *A63B 2208/0228* (2013.01); *A63B 2220/51* (2013.01); *A63B 2220/833* (2013.01); *A63B 2225/09* (2013.01); *A63B 2225/50* (2013.01)

(58) Field of Classification Search
CPC ............ A63B 21/4034; A63B 21/4047; A63B 23/0216; A63B 23/0405; A63B 23/0429; A63B 24/0062; A63B 5/22; A63B 21/00; A63B 21/00181; A63B 21/0628; A63B 21/078; A63B 21/151; A63B 21/159; A63B 21/4011; A63B 21/4035; A63B 23/0211; A63B 23/03508; A63B 23/1209; A63B 23/1263; A63B 23/1281; A63B 24/0003; A63B 24/0087; A63B 71/0622; A63B 2023/003; A63B 2024/0093; A63B 2071/0658; A63B 2208/0204; A63B 2208/0214; A63B 2208/0228; A63B 2220/51; A63B 2220/833; A63B 2225/09; A63B 2225/50; G16H 20/30; G16H 40/63; G16H 50/30
See application file for complete search history.

(56) References Cited

U.S. PATENT DOCUMENTS

| | | | |
|---|---|---|---|
| 4,571,682 A | 2/1986 | Silverman et al. | |
| 5,004,230 A | 4/1991 | Jones | |
| 5,011,142 A * | 4/1991 | Eckler | A63B 21/00072 |
| | | | 482/5 |
| 5,103,404 A | 4/1992 | McIntosh | |
| 5,260,870 A | 11/1993 | Tsuchiya | |
| 5,569,120 A | 10/1996 | Anjanappa et al. | |
| RE35,598 E | 9/1997 | Sadoff | |
| 5,722,921 A | 3/1998 | Simonson | |
| 5,830,116 A | 11/1998 | Gautier | |
| 6,159,131 A | 12/2000 | Pfeffer | |
| 6,296,595 B1 | 10/2001 | Stark et al. | |
| 6,375,598 B1 | 4/2002 | Frame | |
| 6,436,058 B1 | 8/2002 | Krahner et al. | |
| 6,515,593 B1 | 2/2003 | Stark et al. | |
| 6,561,951 B2 | 5/2003 | Cannon | |
| 6,582,342 B2 | 6/2003 | Kaufman | |
| 6,595,901 B2 | 7/2003 | Reinbold et al. | |
| 6,643,385 B1 | 11/2003 | Bravomalo | |
| 6,746,370 B1 | 6/2004 | Fleming | |
| 6,872,187 B1 | 3/2005 | Stark | |
| 7,063,644 B2 | 6/2006 | Albert et al. | |
| 7,070,539 B2 | 7/2006 | Brown et al. | |
| 7,090,623 B2 | 8/2006 | Stewart | |
| 7,101,327 B1 | 9/2006 | Baumler | |
| 7,182,719 B2 | 2/2007 | Tuller | |
| 7,371,216 B2 | 5/2008 | Weyand et al. | |
| 7,618,347 B2 | 11/2009 | Yeo et al. | |
| 7,666,118 B1 | 2/2010 | Anthony | |
| 7,938,760 B1 * | 5/2011 | Webber | A63B 21/15 |
| | | | 482/137 |
| 8,187,153 B2 | 5/2012 | Douglas et al. | |
| 8,388,499 B1 | 3/2013 | Rindfleisch | |
| 8,475,338 B2 | 7/2013 | Greenhill et al. | |
| 8,591,386 B2 | 11/2013 | Meyer et al. | |
| 8,870,720 B1 | 10/2014 | Webber et al. | |
| 8,900,097 B1 | 12/2014 | Griggs et al. | |
| 9,028,433 B2 | 5/2015 | Stephen et al. | |
| 9,050,496 B2 | 6/2015 | Towley et al. | |
| 2002/0072655 A1 | 6/2002 | Pfeffer | |
| 2002/0091039 A1 | 7/2002 | Reinhold et al. | |
| 2002/0128119 A1 | 9/2002 | Arai | |
| 2003/0013071 A1 | 1/2003 | Thomas | |
| 2003/0032524 A1 | 2/2003 | Lamar | |
| 2003/0199370 A1 * | 10/2003 | Bucay-Bissu | A63B 21/4031 |
| | | | 482/142 |
| 2004/0077462 A1 | 4/2004 | Brown | |
| 2004/0110602 A1 | 6/2004 | Feldman | |
| 2004/0117214 A1 | 6/2004 | Shea | |
| 2004/0127336 A1 | 7/2004 | Lapcevic | |
| 2004/0198555 A1 | 10/2004 | Anderson et al. | |
| 2005/0020415 A1 | 1/2005 | Reno | |
| 2005/0107726 A1 | 5/2005 | Oyen | |
| 2007/0027006 A1 | 2/2007 | Suiter | |
| 2008/0248926 A1 | 10/2008 | Cole et al. | |
| 2010/0216600 A1 | 8/2010 | Noffsinger et al. | |
| 2010/0234196 A1 | 9/2010 | Shinomiya | |
| 2012/0040799 A1 * | 2/2012 | Jaquish | A63B 23/0355 |
| | | | 482/9 |
| 2014/0094721 A1 | 4/2014 | Diallo | |
| 2015/0141200 A1 | 5/2015 | Murray | |
| 2015/0238801 A1 * | 8/2015 | Meredith | A63B 21/0628 |
| | | | 482/98 |

FOREIGN PATENT DOCUMENTS

| | | |
|---|---|---|
| JP | 2012-143434 A | 8/2012 |
| WO | WO 2010/059061 A1 | 5/2010 |

OTHER PUBLICATIONS

Mookerjee, S. et al., "Comparison of Strength Differences and Joint Action Durations Between Full and Partial Range-of-Motion Bench

(56) References Cited

OTHER PUBLICATIONS

Press Exercise", The Journal of Strength & Conditioning Research 13(1), 1999, pp. 76-81.
The International Bureau of WIPO, International Preliminary Report on Patentability dated Apr. 23, 2008 for International Application No. PCT/US2006/041190.
ISA/US, International Written Opinion dated Aug. 16, 2007 for International Application No. PCT/US2006/041190.
Supplementary Search Report for EP Application No. 06826421.7 dated Aug. 3, 2012.
International Search Report and Written Opinion for International Application No. PCT/US2012/34552 dated Jan. 25, 2013.

* cited by examiner

DEVICES FOR EXERCISE APPARATUSES

CROSS REFERENCE TO RELATED APPLICATIONS

This application is a continuation application of U.S. patent application Ser. No. 15/758,291, entitled "Devices for Exercise Apparatuses," filed Mar. 7, 2018, which is a 371 U.S. National Phase Application of International Patent Cooperation Treaty Application PCT/US2016/052302, filed Sep. 16, 2016, which is a continuation application of U.S. patent application Ser. No. 14/859,085, entitled "Devices for Exercise Apparatuses," filed Sep. 18, 2015, now abandoned, and claims the benefit of U.S. Provisional Patent Application No. 62/329,999, entitled "Devices for Exercise Apparatuses," filed Apr. 29, 2016, each of which is hereby incorporated by reference.

FIELD OF THE DISCLOSURE

The present disclosure relates to devices for exercise apparatuses. More particularly, this disclosure pertains to devices that permit exercisers to experience high intensity loading of muscles and associated kinetic chain tissue in any one of a plurality of positions throughout the entire range of motion on exercise apparatuses, and/or provide actual loading information of exercisers using exercise apparatuses.

BACKGROUND

Studies have shown that maximum loads are important in the development of skeletal muscle and increase of bone mineral density. In 2004, the Surgeon General's Report on Bone Health and Osteoporosis (See, Chapter 9) stated: "Increases in bone mineral density, to prevent or reverse the effects of osteoporosis, are stimulated by maximum loading on the musculoskeletal system." Zatsiorsky and Kraemer, in their 2006 book, Science and Practice of Strength Training (P. 50), explained the difference between the two different types of muscular growth: "sarcoplasmic hypertrophy of muscle fibers is characterized by the growth of sarcoplasm (semifluid interfibrillar substance) and non-contractile proteins that do not directly contribute to the production of muscle force." Stated differently, sarcoplasmic hypertrophy happens when an individual engages in physical movement with load applied.

Conventional exercise or fitness apparatuses, however, provide only fixed or moderated resistance to users. This resistive force is typically derived from the force of gravity acting on one or more masses, or in some cases a hydraulic cylinder where viscous forces restrict the travel of a movable element within the cylinder. In such devices the amount of load applied over the range of motion of the applicable muscle groups worked by the exercise is set prior to the initiation of the exercise. Moreover, because resistance magnitude is determined prior to the performance of the exercise, the only feedback provided to the users by that endeavor is only binary. They are either able to complete the exercise, or find that it is too difficult to perform. In the case of success with the exercise, the user learns that their weakest point in the range of muscle group motion associated with the exercise provides the requisite force needed to satisfy the selected difficulty setting. In the case of failure with the exercise, the user learns that their weakest point in the range of muscle group motion associated with the exercise fails to provide the requisite force needed to the achieve the selected difficulty setting.

Neither of these outcomes reveals the actual maximum amount of force the user may exert for that exercise in their weakest point in the range of muscle group motion associated with the exercise, or, for that matter, the amount of force they could exert at any other point in the range of motion associated with the exercise. Because muscles fatigue in response to high loads, it is not feasible to ascertain one's maximum capacity in one's weakest range of motion by starting with a small load and repeating the exercise at ever increasing loads. After several trials, the fatigued muscle is unable to approach its previous maximum load.

Furthermore, conventional exercise or fitness apparatuses do not provide users with actual loading information, in particular, the maximum force exertion at any point in the range of user motion associated with a particular exercise.

Thus, what are needed in the art are devices that can permit exercisers to exert high load (e.g., force) or highest possible load in any one of a plurality of positions throughout the entire range of user motion associated with an exercise apparatus without first passing through a weak point in the range of motion, and can provide exercisers with actual loading information on such exercises.

SUMMARY

The present disclosure addresses the preceding and other shortcomings of the prior art by providing a device that can be installed in an exercise apparatus to fix the loading interface of the exercise apparatus at any one of a plurality of functional positions in the functional range of the loading interface, thereby allowing the exerciser to exert high or highest possible load in any one of a plurality of positions throughout the entire range of motion associated with an exercise.

In some aspects, the device measures (directly or indirectly) the load exerted by the exerciser during the exercise and provides the load information during or after the exercise. In an aspect, the device is configured to be installed in various exercise apparatuses, including but not limited to leg press machines, adjustable cable machines, chest press machines, machine bench presses, vertical lift machines, and core machines.

One aspect of the present disclosure provides a device for an exercise apparatus that includes a loading interface and a frame coupled to the loading interface for performing an exercise. The device includes a linear adjustment system that varies a length of the device so as to move the loading interface of the exercise apparatus to any one of a plurality of functional positions in a functional range of the loading interface. The linear adjustment system has a first end and a second end. The first end of the linear adjustment system is configured to be fixedly connected to one of the loading interface and the frame of the exercise apparatus. The device also includes a sensor having a first side and a second side. The first side of the sensor is fixedly coupled to the second end of the linear adjustment system. The second side of the sensor is configured to be fixedly connected to the other of the loading interface and the frame. For instance, if the first end of the linear adjustment system is fixedly connected to the loading interface, the second side of the sensor is fixedly connected to the frame of the exercise apparatus. If the first end of the linear adjustment system is fixedly connected to the frame, the second side of the sensor is fixedly connected to the loading interface. The sensor measures a force exerted on the linear adjustment system, and outputs a signal in accordance with the force exerted on the linear adjustment system.

Another aspect of the present disclosure provides a device for an exercise apparatus that includes a loading interface and a frame coupled to the loading interface for performing an exercise. The device includes a linear adjustment system that varies a length of the device in a longitudinal direction thereby fixing the loading interface of the exercise apparatus at any one of a plurality of functional positions in a functional range of the loading interface. The linear adjustment system comprises a first end and a second end. The device also includes a sensor coupled to the linear adjustment system. The sensor is configured to measure a force exerted on the linear adjustment system. The sensor has a first side and a second side, with the first side fixedly coupled to the second end of the linear adjustment system. The device further includes a first connector and a second connector. The first connector is configured to fixedly connect the first end of the linear adjustment system to one of the loading interface and the frame of the exercise apparatus. The second connector is configured to fixedly connect the second side of the sensor with the other of the loading interface and the frame of the exercise apparatus. For instance, if the first connector is fixedly connected to the loading interface, the second connector is fixedly connected to the frame of the exercise apparatus. If the first connector is fixedly connected to the frame, the second connector is fixedly connected to the loading interface. In some such embodiments, the device includes a correlating mechanism that correlates a force exerted on the linear adjustment system with a force exerted on the loading interface of the exercise apparatus. The exercise apparatus is any one of a plurality of different types of exercise apparatuses.

With the device installed in the exercise apparatus, the exercise exerts one or more muscle groups of a subject through a range of motion associated with (characterized by) the exercise. The range of motion includes a first subrange that is characterized by a first maximum force that can be exerted by the subject. The range of motion further includes a second subrange that is characterized by a second maximum force that can be exerted by the subject. The second maximum force is greater than the first maximum force. In some embodiments, the range of motion can include any number of subrange over and above the first and second subrange. In some embodiments, the device, or specifically, the linear adjustment system of the device, fixes the loading interface at a position in the functional range of the loading interface that permits the subject to exert a force on the loading interface with the muscle group at a point in the range of motion that is in the second subrange without any requirement of passing through the first subrange.

The preceding and other features of the present disclosure will become further apparent from the detailed description that follows. Such description is accompanied by a set of drawing figures. Numerals of the drawing figures correspond to numerals of the written description with like numerals referring to like features throughout both the written description and the drawing figures.

DETAILED DESCRIPTION

The present disclosure provides devices for exercise apparatuses. The devices can be built into exercise apparatuses when manufacturing the exercise apparatuses or retro-fitted into existing exercise apparatuses. The devices of the present disclosure allow exercisers to experience high intensity loading of muscles in any one of a plurality of positions throughout the entire range of motion associated with an exercise without first passing through a weak position, or weak positions, in the range of motion. Thus, the devices enable exertion of the large amounts of force that are deemed beneficial without the conventional constraint of the weakest positions in the range of motion associated with an exercise on an exercise apparatus. In some embodiments, the devices of the present disclosure also provide load/force measurement data and/or information for display or collection during or after the exercise. The data can be used to guide and encourage exercisers during their exercises, or to design better programs to improve their strength, health and fitness. As used herein, "exerciser", "user", "subject" and "object" are interchangeable.

Figure 1A:
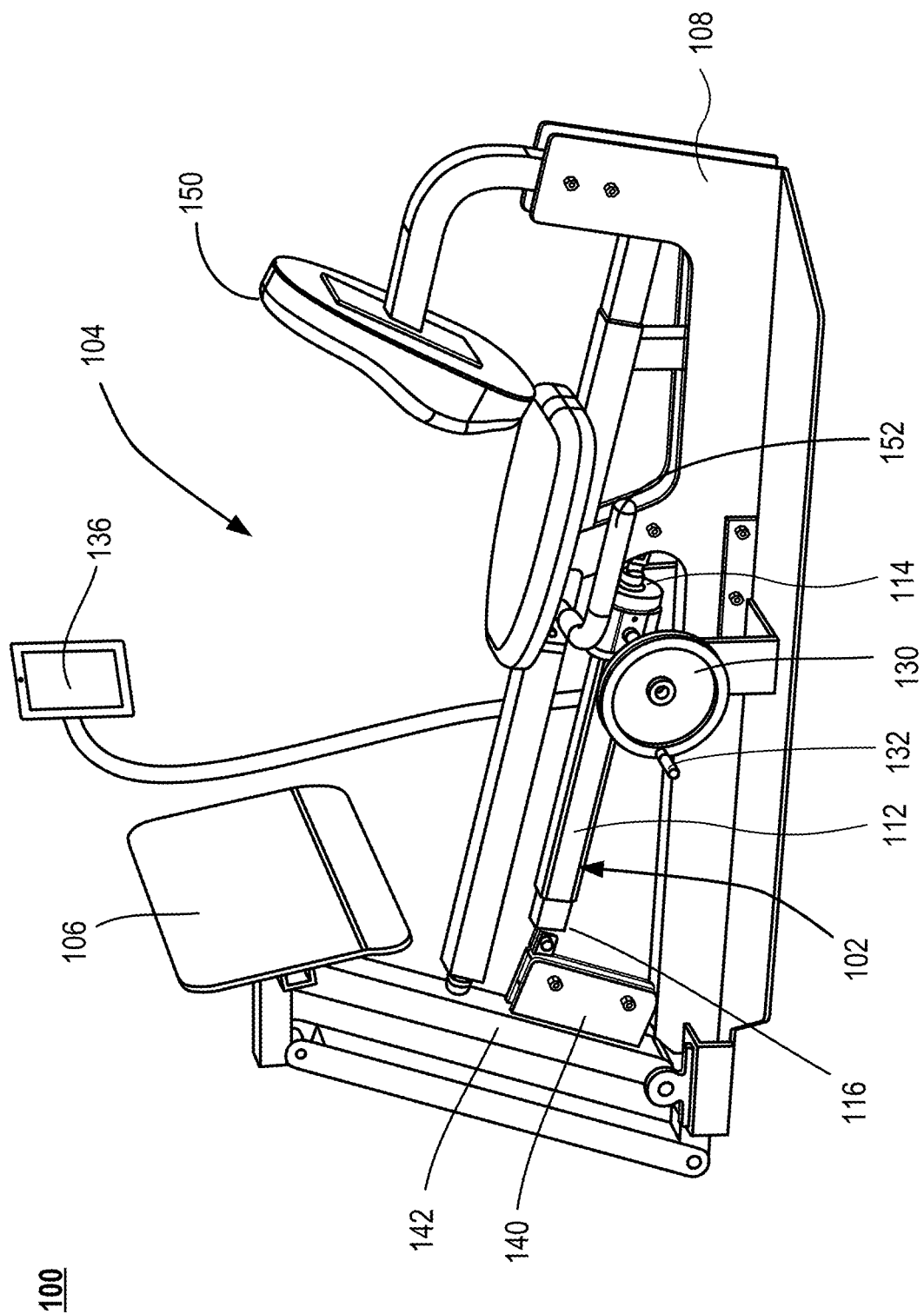
FIG. 1A is a perspective view illustrating a device installed in a first exercise apparatus in accordance with an embodiment of the present disclosure.
Figure 1B:
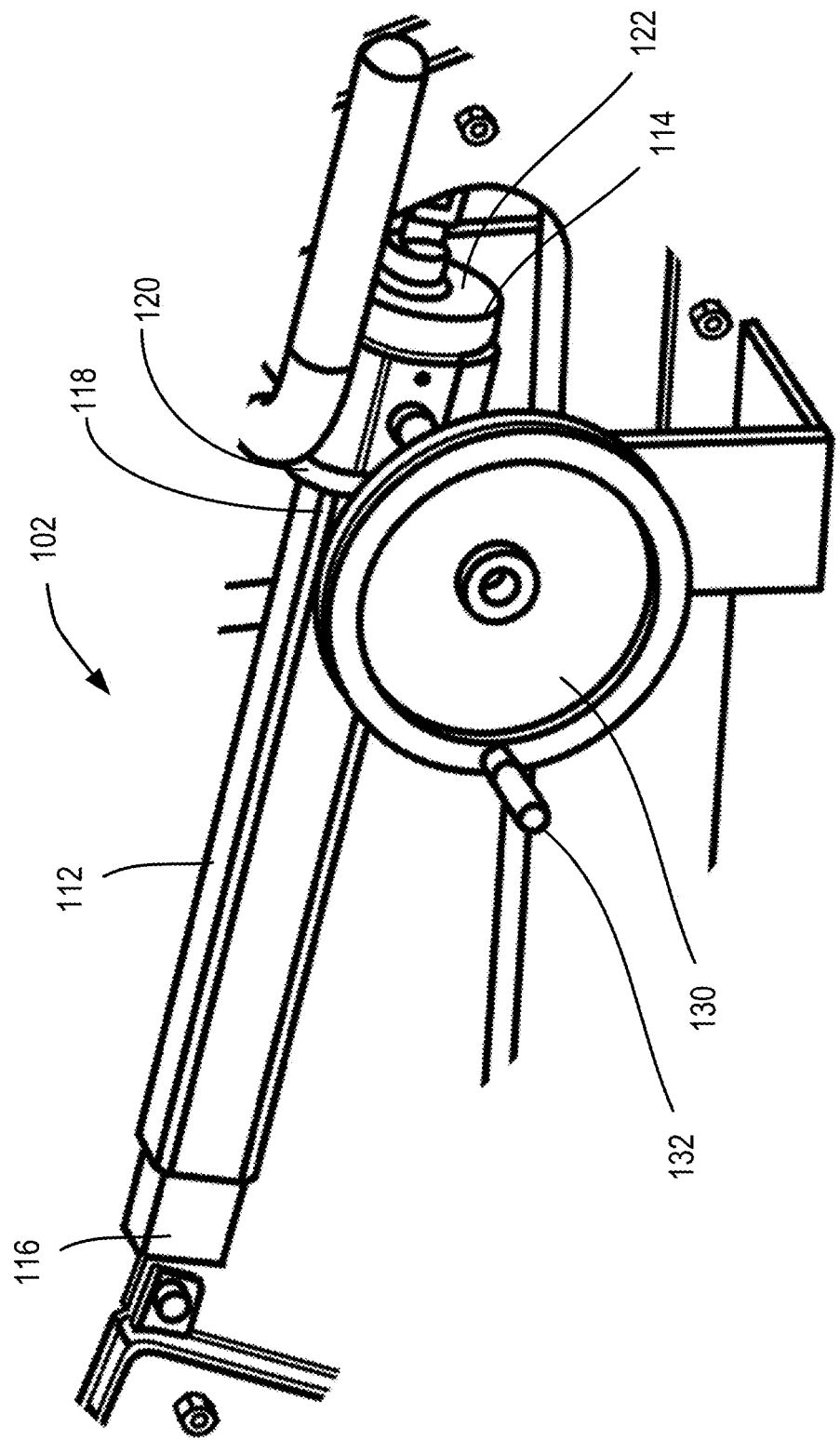
FIG. 1B is a partially enlarged view of FIG. 1A illustrating more detail of the device depicted in FIG. 1A.

Exemplary embodiments of the present disclosure are explained in the paragraphs that follow. Referring to FIGS. 1A-1M, there depicts a device 102 of the present disclosure installed (e.g., built-in or retro-fitted) in an exercise apparatus. By way of illustration, the exercise apparatus in FIGS. 1A-1M is a leg press machine 104. The leg press machine 104 includes a loading interface 106 (e.g., a press plate) and a frame 108 that is coupled to the loading interface 106. During a leg press exercise, an exerciser 110 is usually positioned in the seat 150 and uses hand grips 152. The exerciser 110 places his/her legs on the loading interface 106 and presses the loading interface 106, as illustrated in FIGS. 1C and 1D.

As shown, in some embodiments, the device 102 includes a linear adjustment system 112. In some embodiments, the device 112 also includes a manual or mechanical mechanism, such as one or more of a dial, a handle, a knob, a grip and a button, for adjusting the length of the linear adjustment system. As an example, FIGS. 1A-1M illustrates a dial 130 with a handle 132 protruded from the dial 130 for manually adjusting the length of the linear adjustment system.

The linear adjustment system 112 allows the device 102 to adjust its length in a linear (e.g., longitudinal) direction and to be locked at different lengths as desired. Each such different length acts to fix the loading interface 106 of the exercise apparatus at a different functional position in a plurality of functional positions in the functional range of the loading interface 106. For instance, in some embodiments there are ten or more different lengths at which the linear adjustment system 112 can be adjusted to and locked and a corresponding ten or different functional positions of the loading interface 106. As such, once the device 102 is installed in a selected exercise apparatus such as the leg press machine 104, the device 102 permits an exerciser 110 to exert high load or highest possible load on the loading interface 106 and go to failure using one hundred percent of muscle fiber in any one of a plurality of positions throughout the entire range of motion associated with an exercise associated with the exercise apparatus (e.g., leg press apparatus).

Figure 1C:
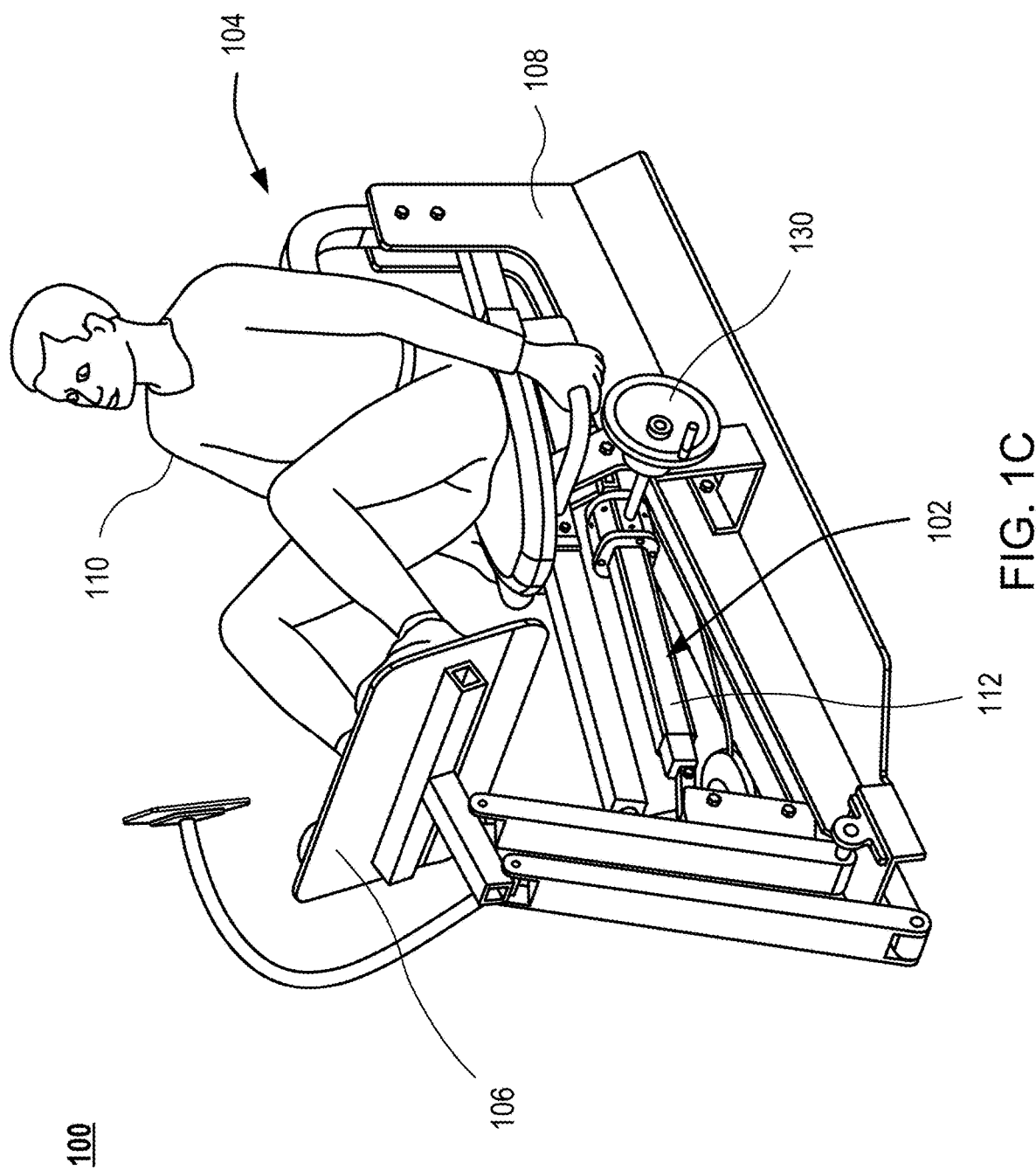
FIG. 1C is a front-left-hand-side perspective view of FIG. 1A, illustrating an exerciser performing an exercise.
Figure 1D:
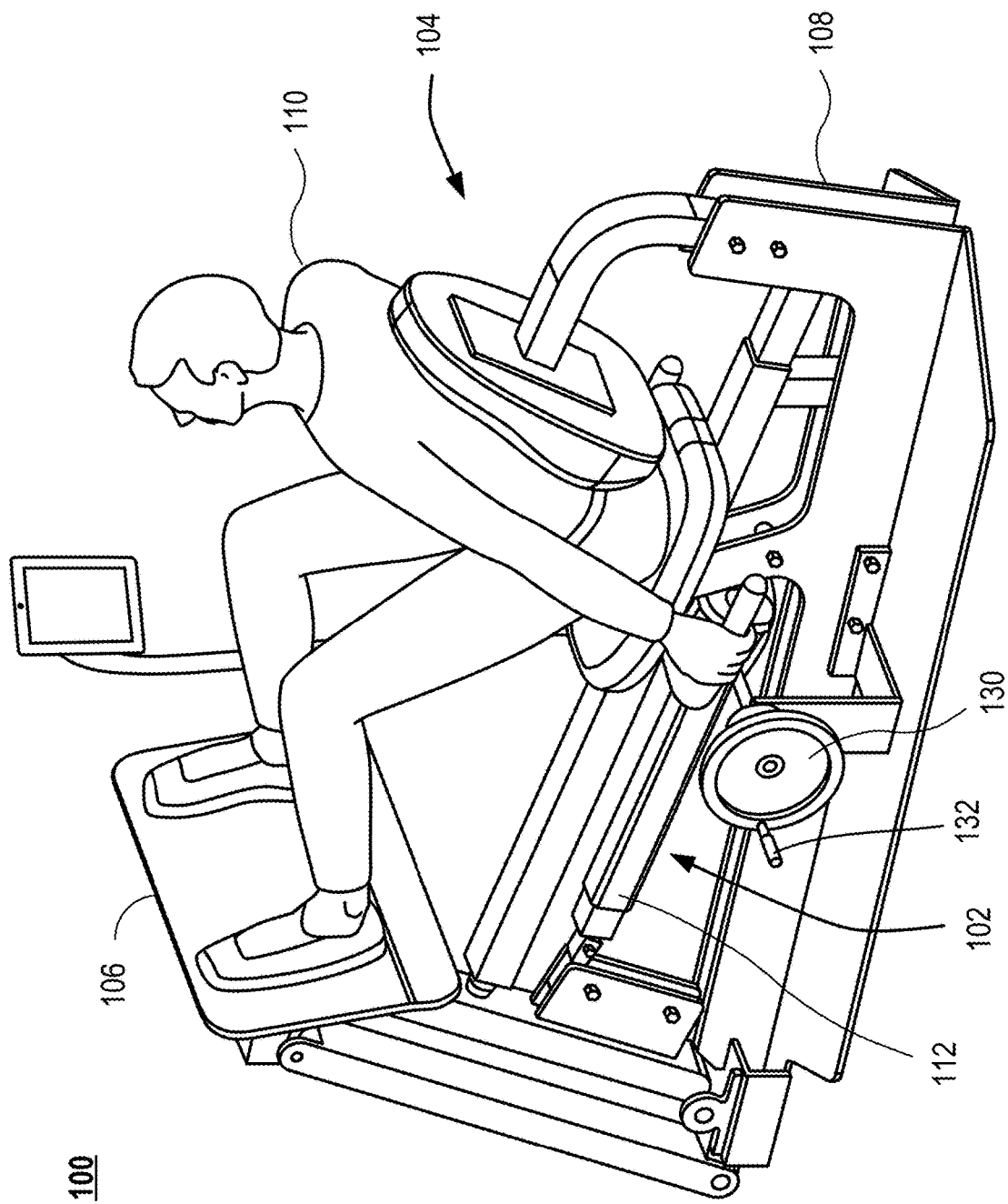
FIG. 1D is a back-left-hand-side perspective view of FIG. 1A, illustrating an exerciser performing an exercise.

For example, referring to FIG. 1C, in some embodiments, an exerciser 110 performs an exercise that exerts a muscle group through a range of motion. In some embodiments, the range of motion includes a first subrange that is characterized by a first maximum force that can be exerted by the exerciser. The range of motion further includes a second subrange that is characterized by a second maximum force that can be exerted by the exerciser. The second maximum force is greater than the first maximum force. The device or the linear adjustment system of the device can fix the loading interface 106 at a functional position in the functional range of the loading interface 106. For instance, the device or the linear adjustment system can fix the loading interface 106 so that it is in the second subrange, and the user does not have to pass through the first subrange to get to the second subrange. At such a position, the exerciser can exert a force on the loading interface 106 with the muscle group at a point in the range of motion that is in the second subrange without any requirement of passing through the first subrange.

Referring to FIG. 1A, when a load or force is exerted on the loading interface 106, the loading interface 106 in turn exerts accordingly a load or force on the linear adjustment system 112. To measure the force exerted on the linear adjustment system 112, the device 102 includes a sensor 114, which is fixedly coupled to the linear adjustment system 112. In some embodiments, the sensor 114 outputs a signal (e.g., analog or digital signal) in accordance with the force exerted on the linear adjustment system.

Referring to FIGS. 1A and 1B, in some embodiments, the linear adjustment system 112 has a first end 116 and a second end 118. The first end 116 is configured to be fixedly connected to one of the loading interface 106 and the frame 108 of the exercise apparatus. The sensor 114 has a first side 120 and a second side 122. In some embodiments, the first side 120 of the sensor 114 is fixedly coupled to the second end 118 of the linear adjustment system 112 as illustrated in FIG. 1B. The second side 122 of the sensor 114 is configured to be fixedly connected to the other of the loading interface 106 and the frame 108 of the exercise apparatus. For example, in the embodiments illustrated in FIGS. 1A-1M, the first end 116 of the linear adjustment system 112 is fixedly connected to the loading interface 106 of the exercise apparatus while the second side 122 of the sensor 114 is fixedly connected to the frame 108 of the exercise apparatus.

It will be appreciated that the placement of the device 102 with respect to the leg press machine 104 or any other exercise apparatus in this disclosure is exemplary and non-exclusive. Since the length of the device 102 can be adjusted and locked as desired, the device 102 can be installed in the exercise apparatus in different locations and connected to different components of the exercise apparatus as long as the device 102 can fix the loading interface 106 at different functional positions and the load exerted on the loading interface 106 can be measured (directly or indirectly). For example, the first end of the linear adjustment system can be fixedly connected to the frame instead of the loading interface 106 or connected to different bars or plates or other structural components of the exercise apparatus.

It will also be appreciated that the first end 116 of the linear adjustment system and the second side 122 of the sensor 114 can be directly or indirectly connected to the loading interface 106 or the frame of the exercise apparatus. For example, the first end of the linear adjustment system and the second side of the sensor 114 can be indirectly connected to the loading interface 106 or the frame of the exercise apparatus through other components such as connectors, plates, brackets, or bars. By way of illustration, FIGS. 1A-1M illustrate the first end 116 of the linear adjustment system 112 indirectly connected to the loading interface 106 of the exercise apparatus through one or more plates 140 and a bar 142.

Figure 2A:
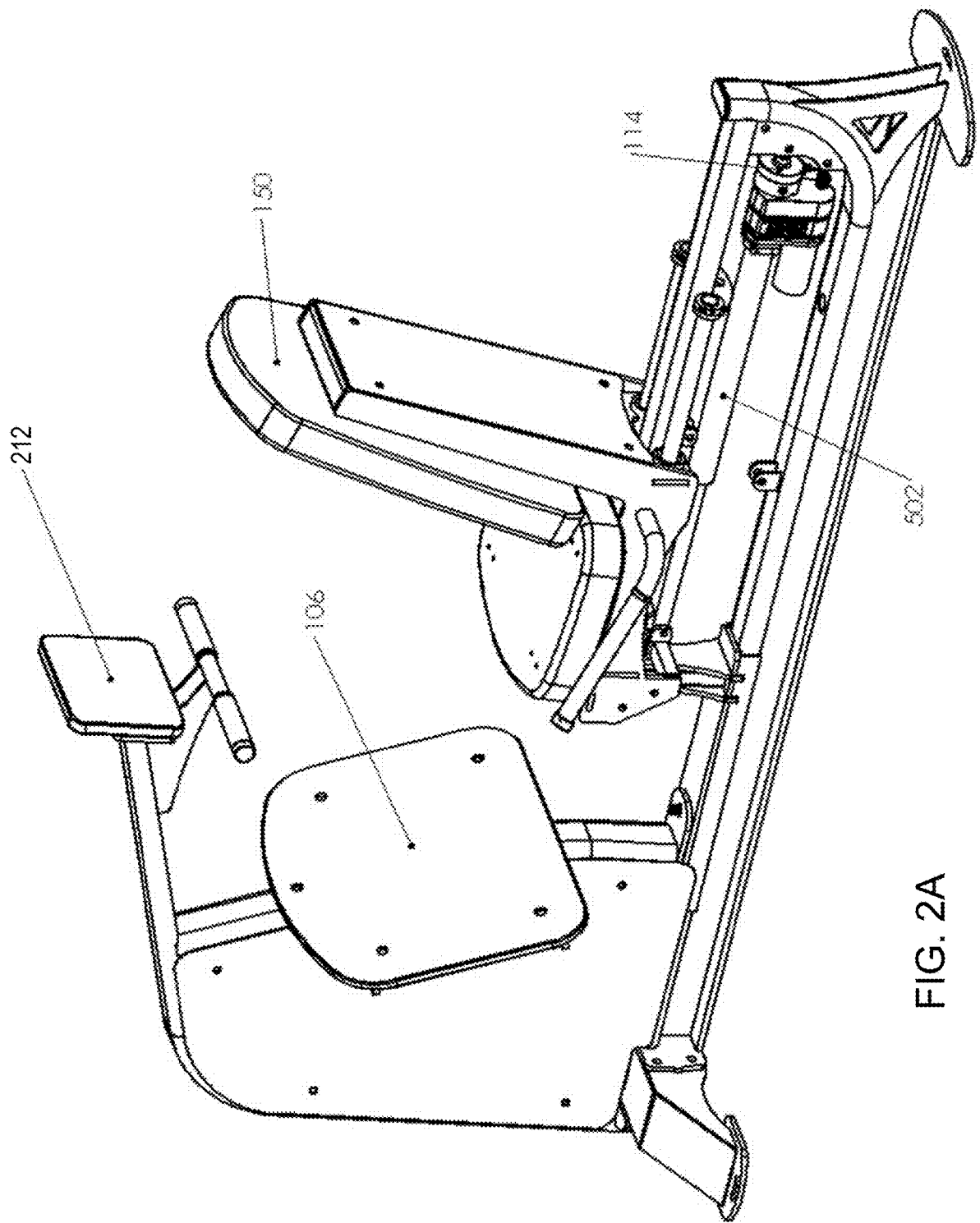
FIG. 2A is a perspective view illustrating a device installed in a second exercise apparatus in accordance with an embodiment of the present disclosure.

It will further be appreciated that the exercise apparatuses in this disclosure are exemplary and non-exclusive. Since the linear adjustment system 112 allows the device 102 to adjust an overall dimension of the device in a linear (e.g. longitudinal) direction, the device 102 can be installed in a variety of different types of exercise apparatuses. As an example, FIG. 2A illustrates the device used with a different leg press machine and the exercise is a leg press exercise. In this embodiment the device 102 includes a linear actuator 502, and a force sensor 114, where the linear actuator 502 acts as the linear adjustment system 112 and permits the movement of the leg press machine seat assembly 150 as a means of adjusting the user's loading position with respect to the loading interface 106. In some embodiments, the movement of the actuator 502 is governed by a user interface displayed on the touchscreen electronic device 212 (monitor device), which also provides graphical and/or numeric feedback on force exerted from the load cell sensor 114.

Figure 2B:
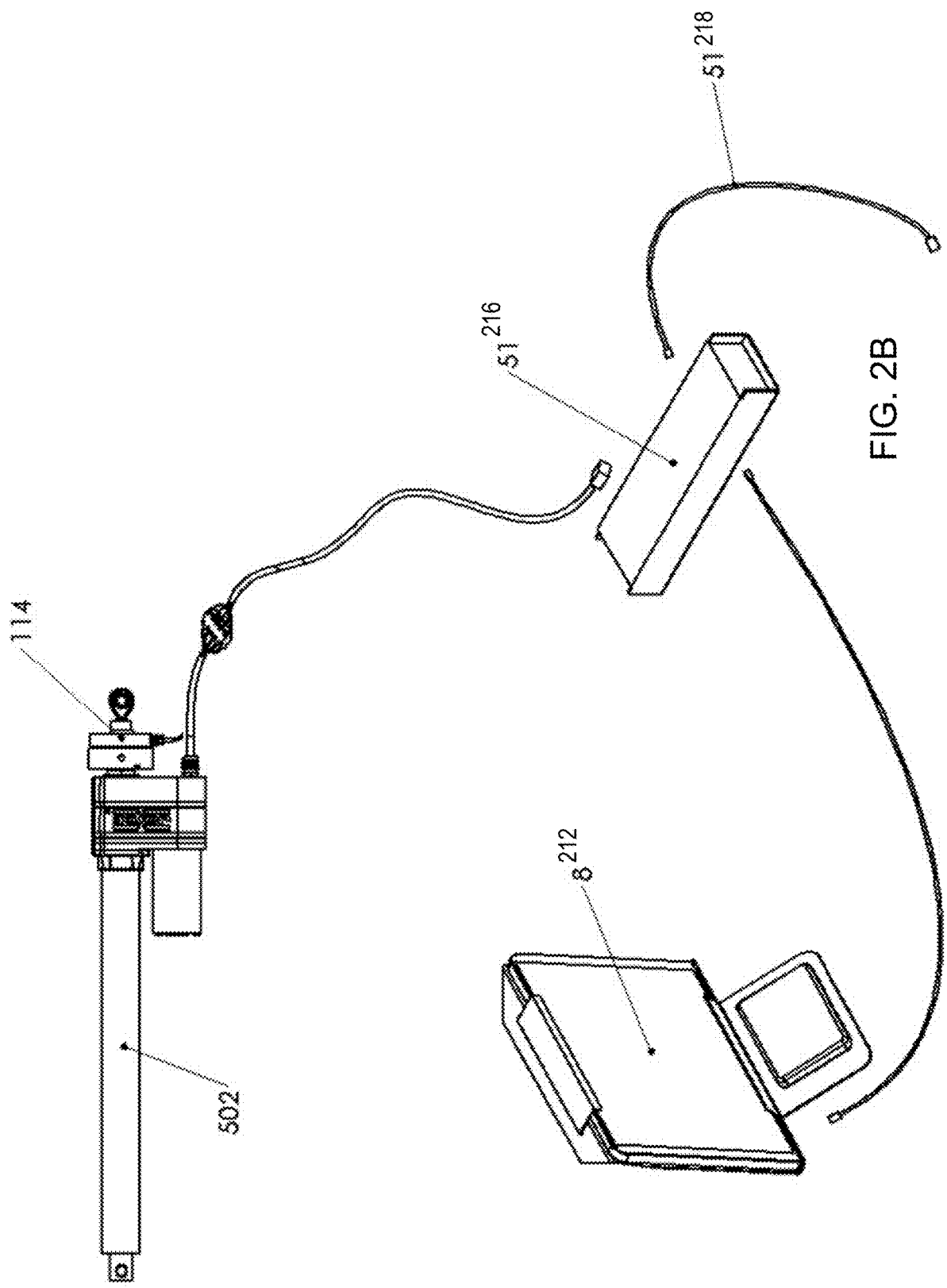
FIG. 2B is a perspective view of the principle system components of the device of FIG. 2A in accordance with some embodiments of the present disclosure.

As further clarification, the embodiment of the device depicted installed on a leg press machine in FIG. 2A is shown in isolation in FIG. 2B. The monitor device 212 which includes the user interface and data display is connected to an embedded electronics component 216, which contains power switching circuitry to control the actuator. In some embodiments the embedded electronics 216 also include a power transformer to provide appropriate voltages to drive the linear actuator 502 and power the electronic device 212. In some embodiments the power input cord 218 which connects to the embedded electronics 216 provides power to the entire system from an earth grounded power source. In some embodiments the force sensor 114 is wired to the embedded electronics 216. In some embodiments the force sensor signal is processed by the embedded electronics 216 and transmitted by wired connection to the electronic device 212. In some embodiments communication between the electronic device 212 and embedded electronics 516 is wireless. In some embodiments the electronic device 212 is powered independently from the embedded electronics 516.

Figure 2C:
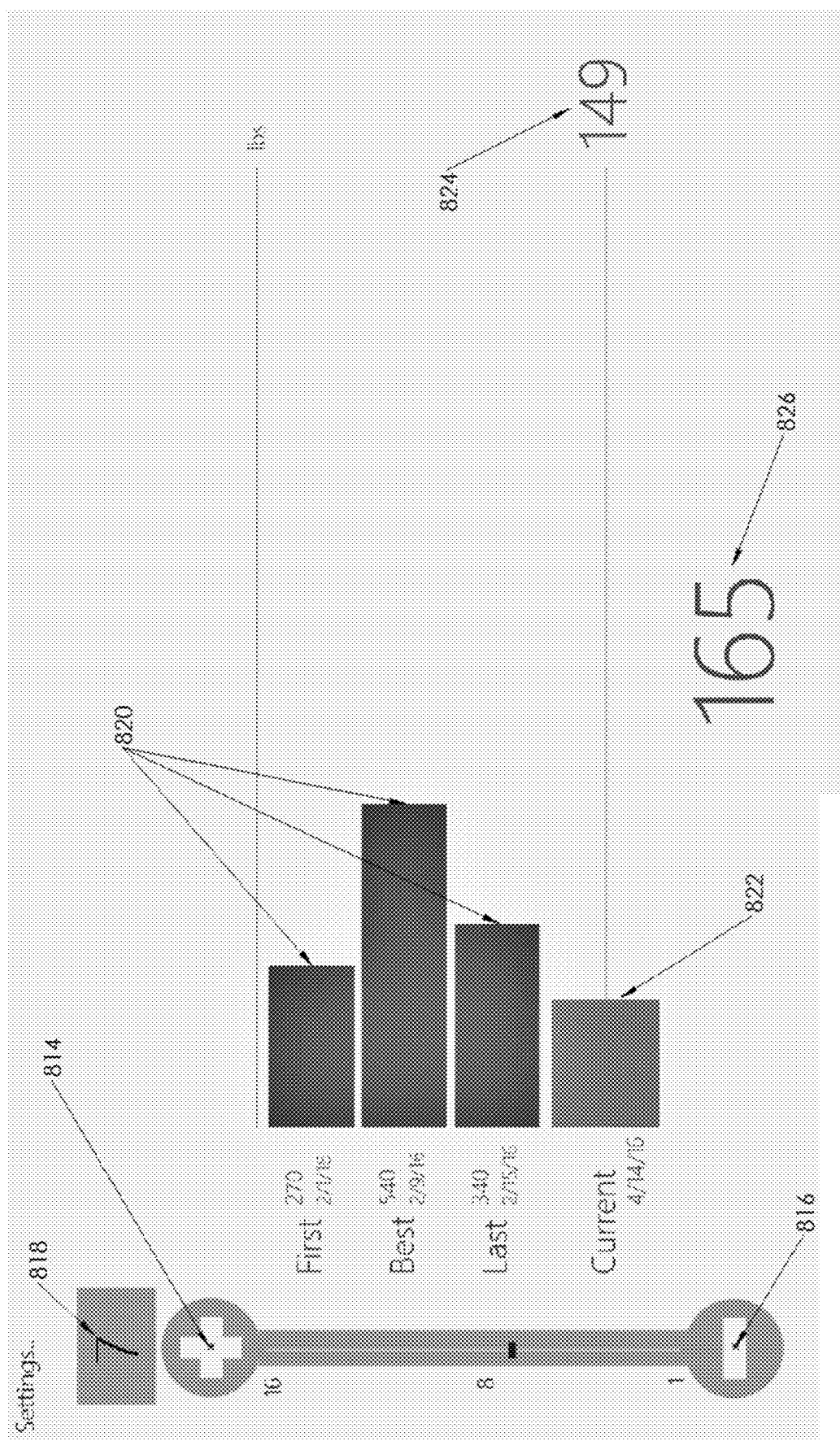
FIG. 2C is a depiction of the user interface associated with the device depicted in FIG. 2A and FIG. 2B in accordance with some embodiments of the present disclosure

FIG. 2C provides as an example of the user interface displayed in some embodiments of the electronic device 212 shown in FIG. 2B. The user interface in FIG. 2C includes an affordance 814 for extending and an affordance 186 for retracting the linear actuator 502 shown in FIG. 2A and FIG. 2B. In some embodiments, the affordance 814 and the affordance 816 are a single slide bar as depicted in FIG. 2C. As such, in some embodiments a single graphic element or physical switch may serve both to retract and extend the actuator 502. The actuator position 818 is also indicated in the example interface of FIG. 2C. Data is provided showing the user's previous first, best, and most recent force productions 820, in conjunction with graphical 822 and numerical 824 display of the instantaneous value of the user's force production. In some embodiments of the present disclosure a metric 826 will be displayed indicating the highest average value of force production in the current exercise session over any time interval of predetermined duration (e.g., of any five consecutive seconds, of any ten consecutive seconds, etc.).

Figure 2D:
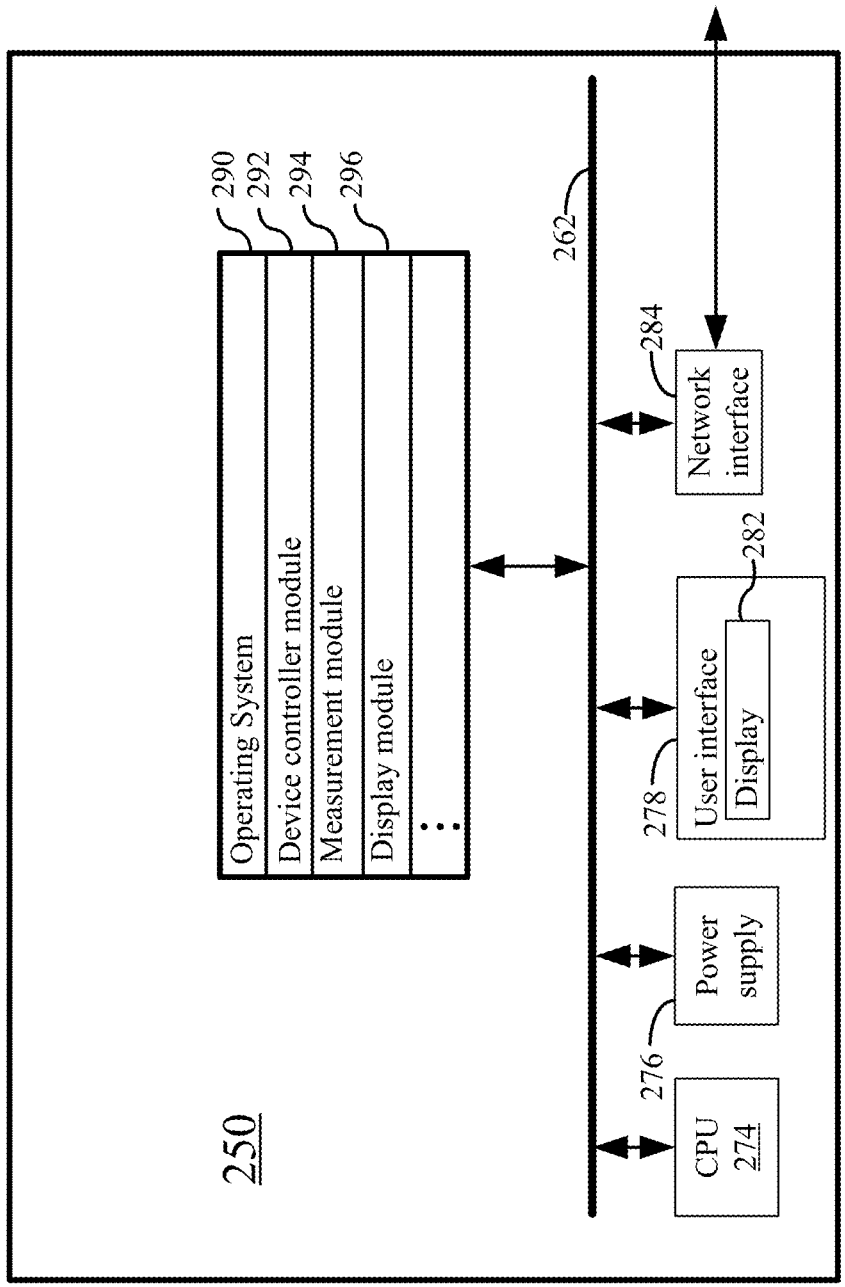
FIG. 2D illustrates a computer system in accordance with an embodiment of the present disclosure.

FIG. 2D illustrates a computer system 250 for processing input data from an exercise apparatus that includes a loading interface and a frame coupled to the loading interface for performing an exercise. Referring to FIG. 2D, in typical embodiments, the computer system 250 comprises one or more processing units (CPU's) 274, a network or other communications interface 284, a user interface (e.g., including a display 282 that doubles, in some embodiments, as an input device) a memory 292 (e.g., random access memory), one or more communication busses 262 for interconnecting the aforementioned components, and a power supply 276 for powering the aforementioned components. Data in memory 292 can be seamlessly shared with non-volatile and volatile memory not shown using known computing techniques such as caching. Memory 292 can include mass storage that is remotely located with respect to the central processing unit(s) 274. In other words, some data stored in memory 292 may in fact be hosted on computers that are external to computer system 250 but that can be electronically accessed by the computer system over an Internet, intranet, or other form of network or electronic cable using network interface 284. The memory 92 of analysis computer system 250 stores:

an operating system 290 that includes procedures for handling various basic system services;
a device controller module 292 for sending step function instructions to a linear adjustment system 112 that fixes the loading interface 106 of an exercise apparatus at any one of a plurality of functional positions in a functional range of the loading interface, where the linear adjustment system 112 comprises a first end 116 and a second end 118, and the first end 116 is configured to be fixedly connected to one of the loading interface 106 and the frame 108 of the exercise apparatus, where the exercise exerts a muscle group of a subject through a range of motion, the range of motion including a first subrange that is characterized by a first maximum force that can be exerted by the subject, the range of motion further including a second subrange that is characterized by a second maximum force that can be exerted by the subject, the second maximum force is greater than the first maximum force, and where the linear adjustment system, responsive to the step function instructions, fixes the loading interface at a position in the functional range of the loading interface that permits the subject to exert a force on the loading interface with the muscle group at a point in the range of motion that is in a second subrange without any requirement of passing through the first subrange;
a measurement module 294 for obtaining a measurement of a force exerted on the linear adjustment system 112 from a sensor 114, where the sensor 114 comprises a first side 120 fixedly coupled to the second end 118 of the linear adjustment system 112 and a second side 122 configured to be fixedly connected to the other of the loading interface 106 and the frame 108; and
a display module 296 for outputting to a monitor device the measured force on the linear adjustment system or a force exerted on the loading interface of the exercise apparatus that is calculated from the measured force on the linear adjustment system and/or any of the information illustrated in FIG. 2C.

In some implementations, one or more of the above identified data elements or modules of the computer system 250 are stored in one or more of the previously disclosed memory devices, and correspond to a set of instructions for performing a function described above. The above identified data, modules or programs (e.g., sets of instructions) need not be implemented as separate software programs, procedures or modules, and thus various subsets of these modules may be combined or otherwise re-arranged in various implementations. In some implementations, the memory 92 optionally stores a subset of the modules and data structures identified above. Furthermore, in some embodiments the memory 92 stores additional modules and data structures not described above.

In some embodiments, the linear adjustment system 112 comprises a linear actuator whose extension and contraction is controlled by a peripheral electronic device comprising a power switching circuit or a servo motor controller thereby causing the linear adjustment system to move the loading interface to a functional position, in the plurality of functional positions, that the linear adjustment system fixes the loading interface, responsive to the step function instructions provided by the device controller module 292.

In some embodiments, the computer system 250 stores instructions for determining an osteogenic loading based on the measured force on the linear adjustment system or the force exerted on the loading interface that is calculated from the measured force on the linear adjustment system.

In some embodiments, the computer system 250 stores instructions for providing an affordance on a display (e.g., 814/816 of FIG. 2C) that allows a user to select a functional position in the plurality of functional positions for the loading interface. Further, responsive to user interaction with the affordance, the device controller module 292 sends step function instructions to a linear adjustment system 112.

In some embodiments the display module 296 displays a current functional position in the plurality of functional positions of the loading interface 106.

In some embodiments the display module 296 provides a numerical or graphical comparison of a user's current force output in a current session with the exercise apparatus that is fixed by the linear adjustment system to any of (i) the magnitude of a force generated by the same user in a session with the exercise apparatus immediately prior to a current session with the exercise apparatus by the user, (ii) in a prior session with the exercise apparatus for which a highest force was achieved by the user, and (iii) the first ever session the user had with the exercise apparatus.

Figure 3:
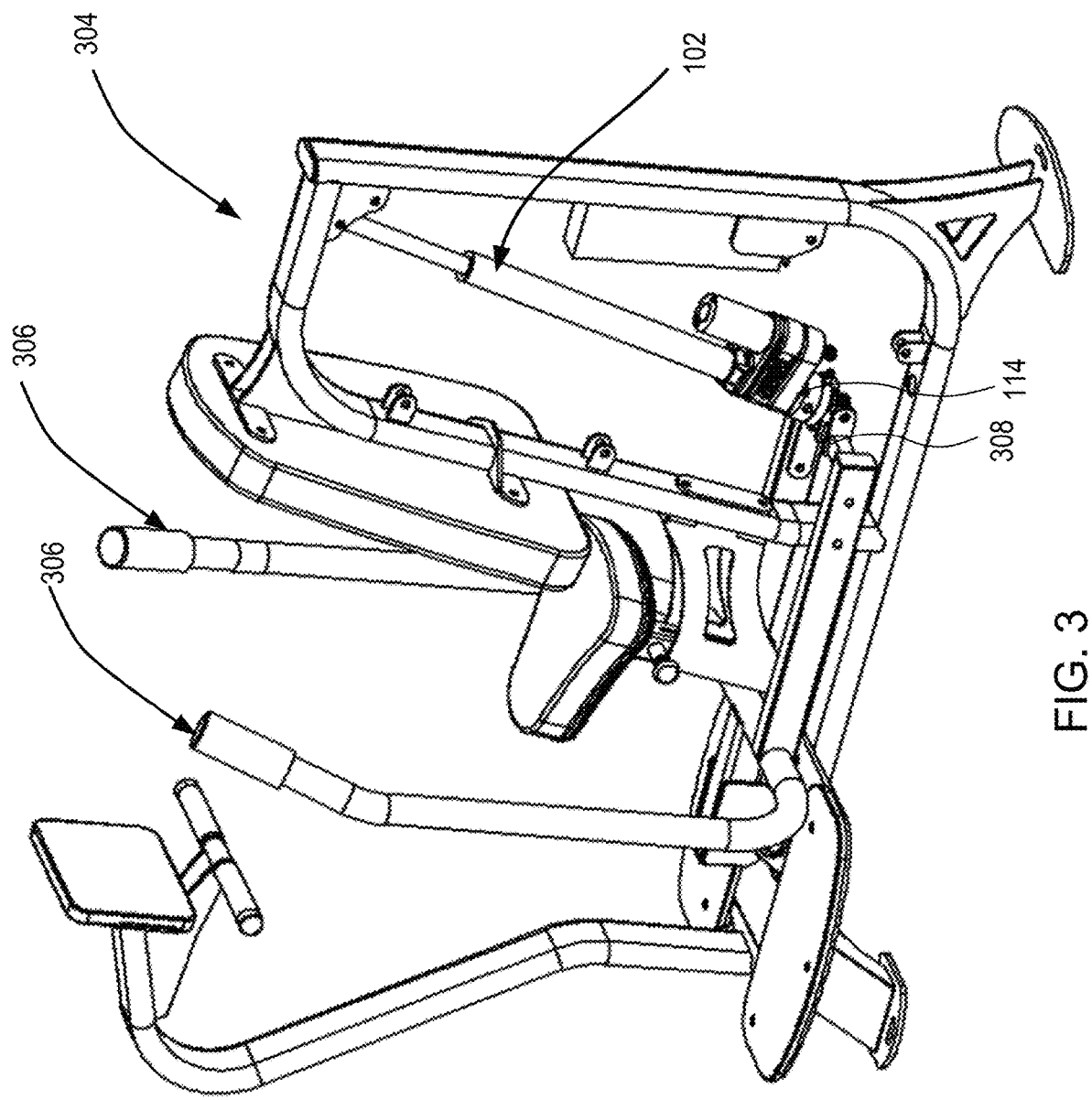
FIG. 3 is a perspective view illustrating a device installed in a third exercise apparatus in accordance with an embodiment of the present disclosure.
Figure 4:
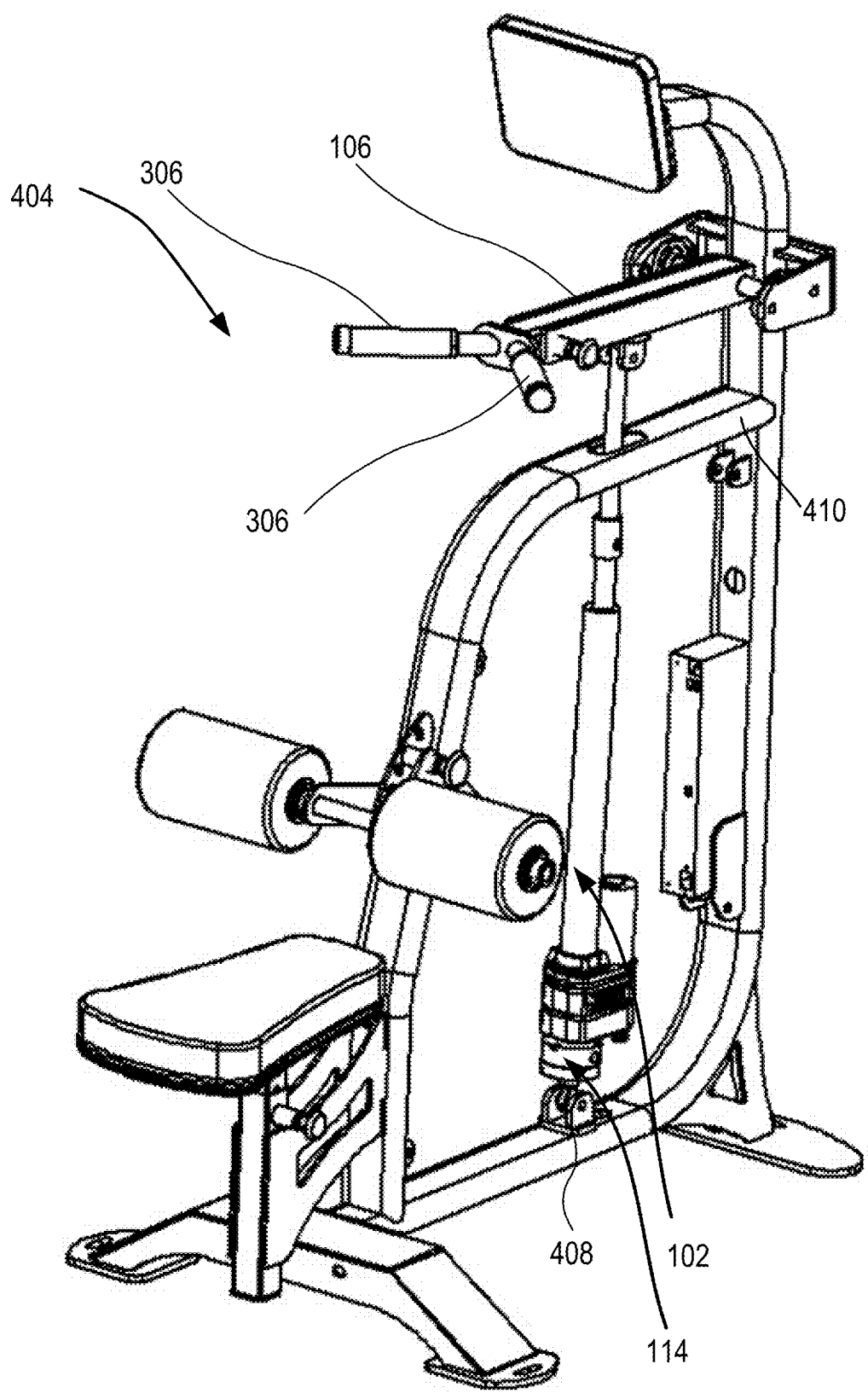
FIG. 4 is a perspective view illustrating a device installed in a fourth exercise apparatus in accordance with an embodiment of the present disclosure.
Figure 5:
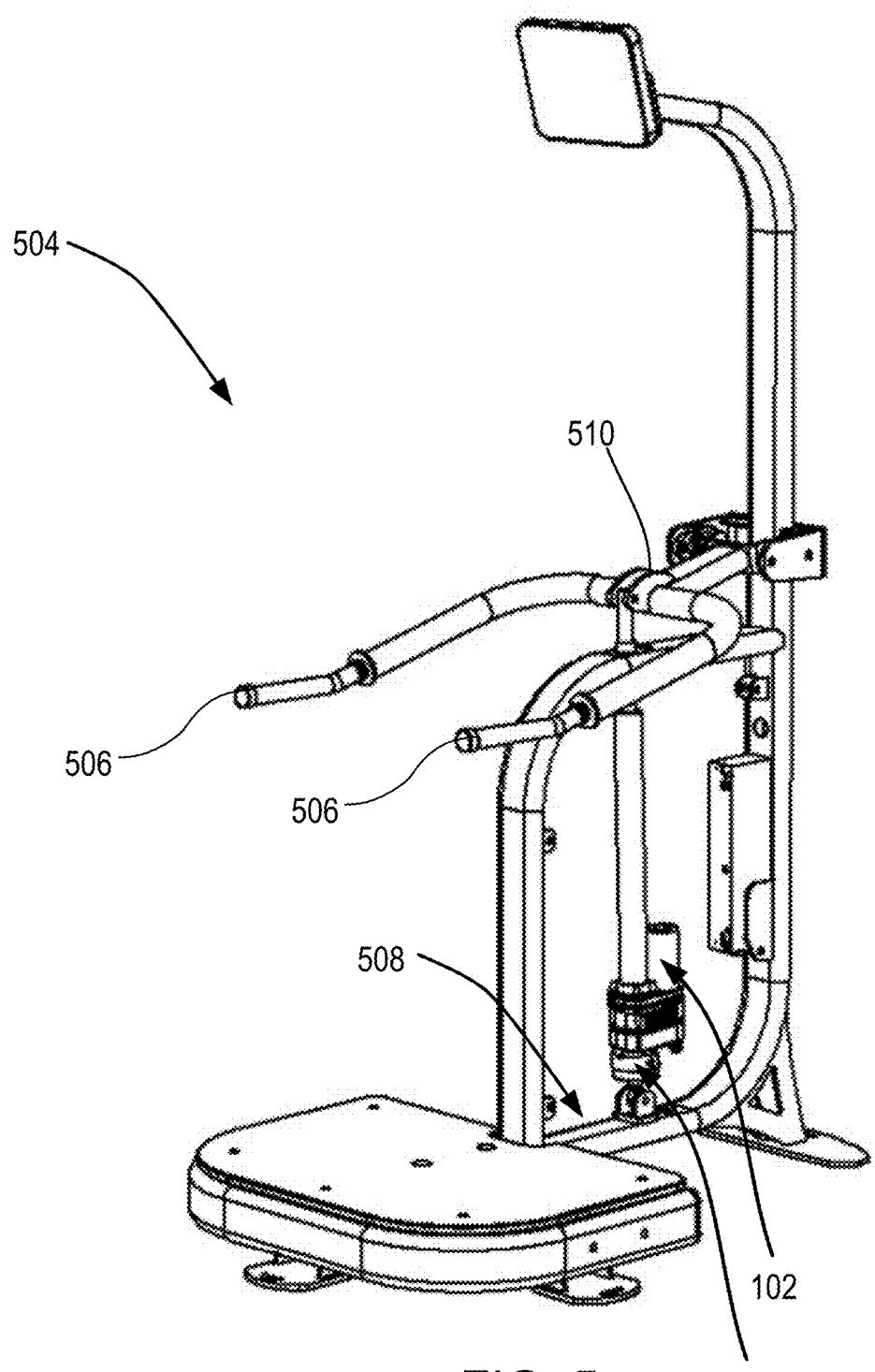
FIG. 5 is a perspective view illustrating a device installed in a fifth exercise apparatus in accordance with an embodiment of the present disclosure.

As another example, FIG. 3 illustrates the device 102 used with a chest press machine 304 and the exercise is a chest press exercise. As a further example, FIG. 4 illustrates the device 102 used with a core machine 404 and the exercise is an abdominal exercise. As a yet further example, FIG. 5 illustrates the device 102 used with a vertical lift machine 504 and the exercise is a vertical lift exercise.

Referring to FIG. 3, similar to the leg press machine 104 in FIGS. 1A-1M, the placement of the device 102 with respect to the chest press machine 304 (FIG. 3), the core machine 404 (FIG. 4) or the vertical lift machine 504 (FIG. 5), is exemplary and non-exclusive. In addition, similar to the leg press machine 104 in FIGS. 1A-1M, the device 102 can be placed in any appropriate position and connected to different components of the chest press machine 304, the core machine 404 or the vertical lift machine 504. In some embodiments, the device 102 replaces a hydraulic cylinder or a weight stack in the exercise apparatus as illustrated in FIGS. 2 and 3. In some embodiments, the device 102 serves as a rigid beam to fix a lever arm or a movable element of the loading interface 106 of the exercise apparatus illustrated in FIG. 4.

In some embodiments, the exercise apparatus is an adjustable cable machine and the exercise is a single-arm cable row, a V-grip cable row, a close-grip lateral pulldown, a kneeling lateral pulldown, a face pule external rotation, a standing rotational chop, a cable crunch, a half-kneeling rotational chop, a cable overhead triceps extension, a one-arm cable lateral raise, a 30-degree lateral pulldown, a rope pressdown, a 90-degree cable external rotation, a behind-the back one-arm cable curl, a knelling rotational chop, a cable external rotation, a kneeling stability reverse chop, a cable core press, a straight-arm pulldown, a cable pressdown, a standing cable pullover, a seated cable row, a half-kneeling stability chop, a single-arm cable chest press, a standing side crunch, a face pull, a cable front raise, a kneeling oblique cable crunch, or a reverse-grip.

The loading interface 106 can take a variety of forms. For example, the loading interface 106 includes one or more leg press plates 106 as illustrated in FIGS. 1A-1M, one or more chest-press loading interfaces 306 as illustrated in FIG. 3, one or more core-pull loading interfaces 306 as illustrated in FIG. 3, or one or more vertical-lift loading interfaces 506 as illustrated in FIG. 5.

In some embodiments, the device 102 further includes a correlation mechanism that correlates the measured force on the linear adjustment system to an actual force exerted on the loading interface from the exercise. In some embodiments, the correlation mechanism includes, but is not limited to, tables, charts, curves, or polynomials, in which the two operating variables are (i) the amount of force detected by the sensor 114 and (ii) the position of the linear adjustment system 112. In an embodiment, the correlation mechanism includes a predetermined master table for the exercise apparatus, such as the predetermined master table 808 illustrated in FIG. 9. The predetermined master table 808 includes a set of forces measured by the sensor and corresponding actual forces exerted on the loading interface for each functional position in the plurality of functional positions and for each measured force in a plurality of measured weights forces. In some embodiments, the correlation mechanism is embedded in the sensor 114. For instance, in some embodiments the master table 808 will have a plurality of cells, each cell indexed by (i) a measured force on the sensor and (ii) a functional position. Further, the cell with have a value, this value representing the actual force given the indices (i) and (ii).

Figure 6:
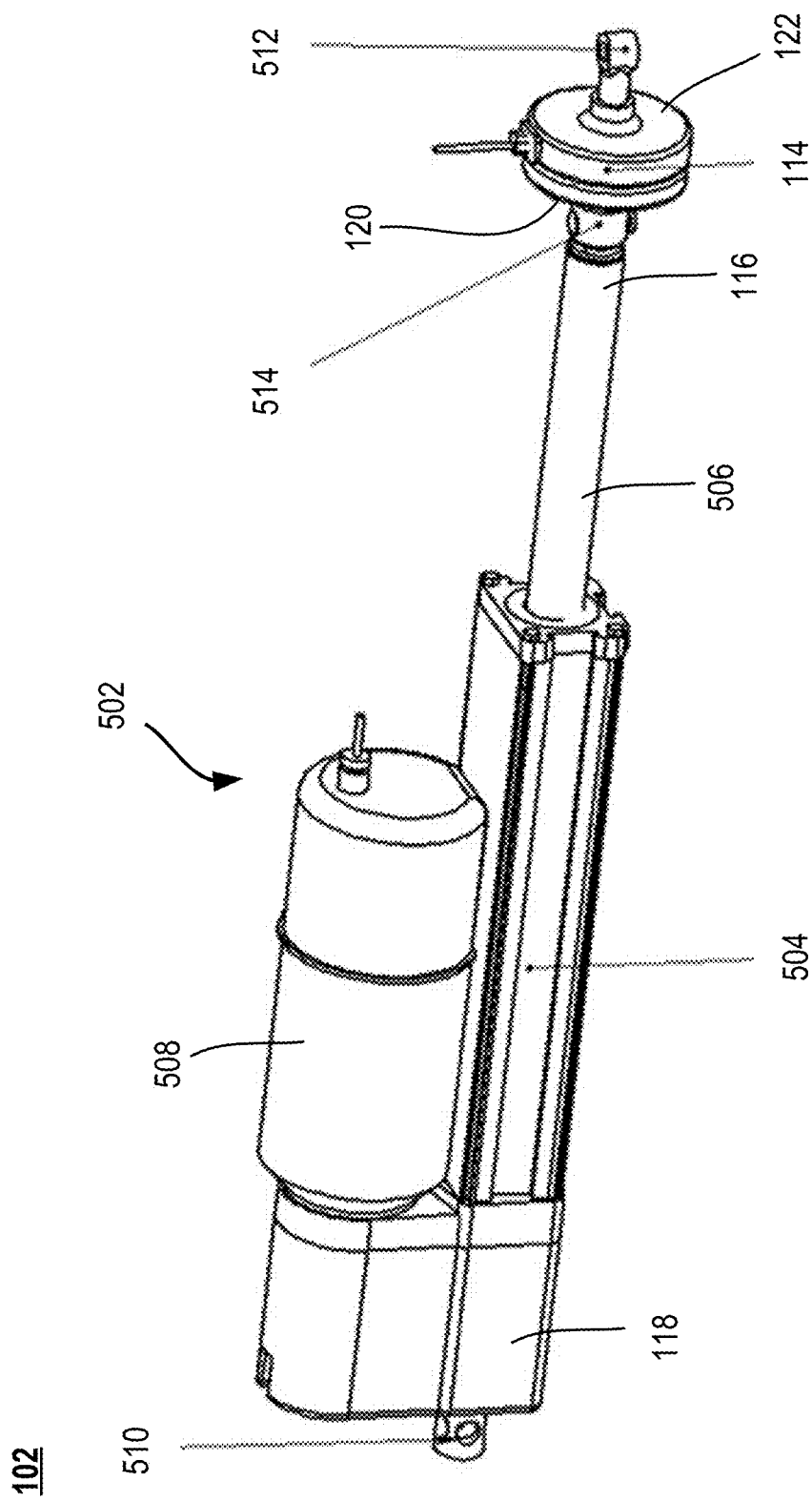
FIG. 6 is a perspective view illustrating a device in accordance with an embodiment of the present disclosure.
Figure 7:
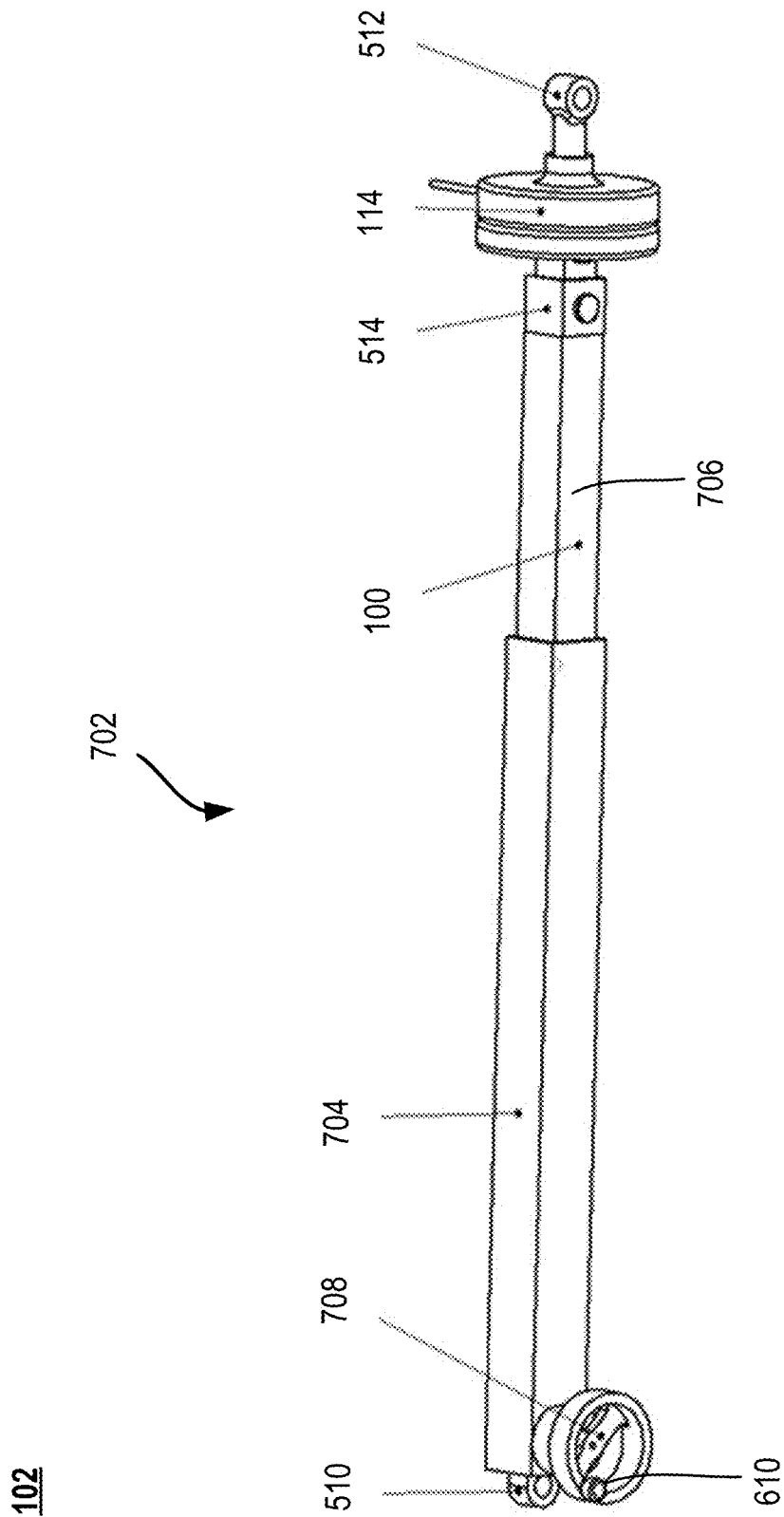
FIG. 7 is a perspective view illustrating a device in accordance with another embodiment of the present disclosure.
Figure 8:
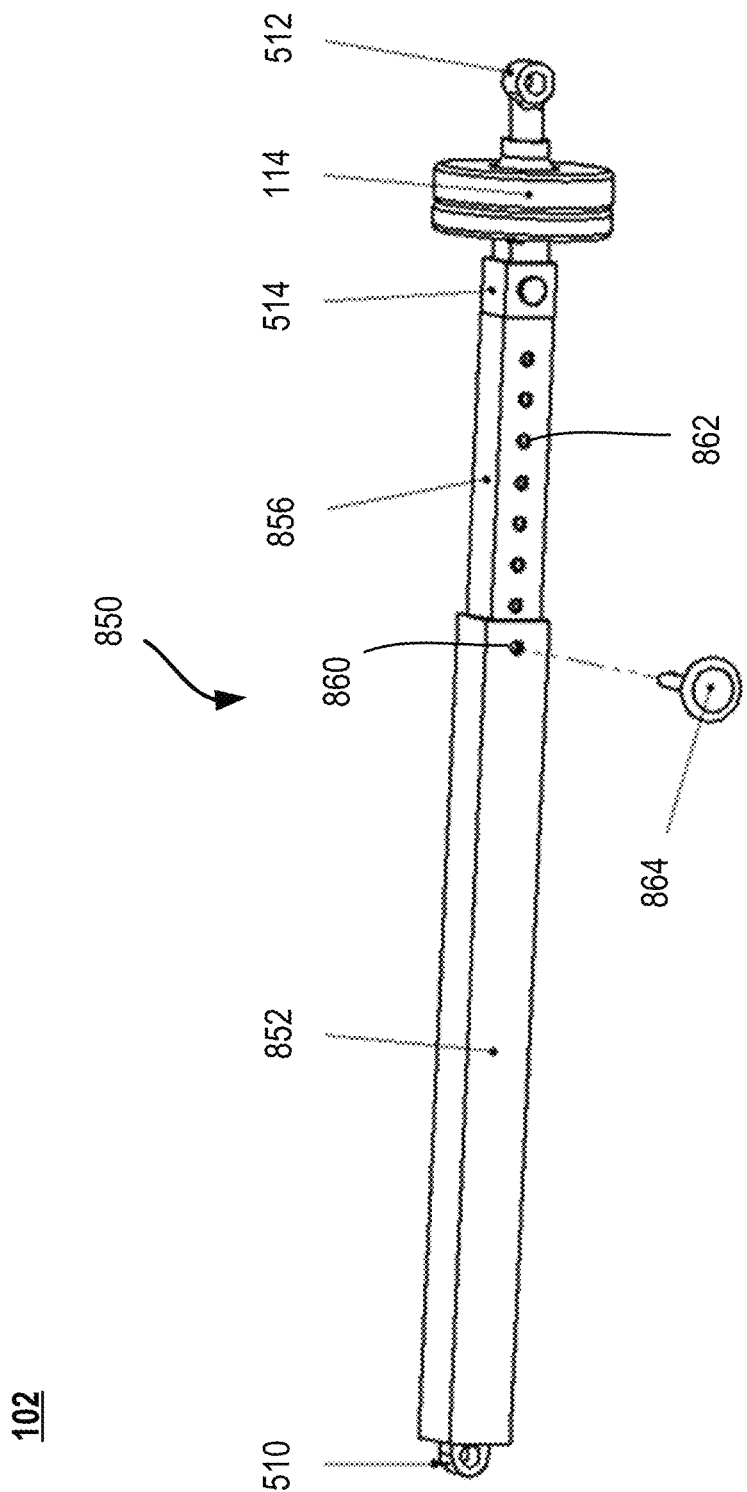
FIG. 8 is a perspective view illustrating a device in accordance with still another embodiment of the present disclosure.

Referring now to FIGS. 6-8, there are depicted exemplary linear adjustment systems of the device 102 in accordance with some embodiments of the present disclosure. It will be appreciated that these embodiments are illustrative and non-limiting. Other systems, mechanisms, or structures can be used provided that such systems, mechanisms, or structures facilitate the adjustment of the loading interface of an exercise apparatus and lock the loading interface of the exercise apparatus at different functional positions in the functional range of the loading interface.

As shown in FIG. 6, in some embodiments, the linear adjustment system is a linear actuator 502. The linear actuator 502 includes a fixed portion 504 and an extendable portion 506 axially aligned with the fixed portion. The extendable portion 506 is moveable with respect to the fixed portion 504 in the longitudinal direction of the linear actuator 502. In an embodiment, the fixed portion 504 and the extendable portion 506 are concentric. In another embodiment, the fixed portion 504 and the extendable portion 506 are concentric and have substantially same cross-sections in shape. In some embodiments, the extendable portion has a nominal diameter smaller than the fixed portion. In one embodiment, the fixed portion is hollow and the extendable portion is slidably disposed in the fixed portion.

The linear actuator 502 further includes a locking mechanism 508 to lock the extendable portion at a selected position with respect to the fixed portion. The locking mechanism 508 is activated electrically, pneumatically, hydraulically or mechanically.

In some embodiments, the device 102 includes one or more connectors. For example, FIG. 6 illustrates the device 102 including a first connector 510 and a second connector 512. The first connector 510 is disposed at the first end or the second end of the linear adjustment system (e.g., the linear actuator 502) for fixedly connecting that end of the linear adjustment system with the loading interface or the frame of an exercise apparatus. By way of illustration, FIG. 5 shows the first connector 510 disposed at the second end 118 of the linear adjustment system, and FIGS. 1A-1M show the first connector disposed at the first end 116 of the linear adjustment system. The second connector 512 is disposed on the second side 122 of the sensor 114 for fixedly connecting the second side 122 of the sensor 114 with the loading interface or the frame of an exercise apparatus. In some embodiments, the first connector 510 and/or the second connector 512 are a tang, a clevis, a clamp, a fastener, a pin, a screw, a bolt, a ring, or the like. In some embodiments, the device 102 further includes a third connector 514 disposed between the linear adjustment system and the sensor. The third connector 514 fixedly connects the other end of the linear adjustment system with the first side 120 of the sensor 114.

Referring back to FIGS. 1A-5, in some embodiments, connection of the first end 116 of the linear adjustment system 112 to the loading interface 106 or the frame 108 is achieved by connecting the first end of the linear adjustment to one or more components in the exercise apparatus that extend from the loading interface 106 or the frame 108. For example, FIGS. 1A-5 illustrate the connection through one or more plates and/or bars (e.g., 140, 142, 410, 510) in the exercise apparatus that extend from the loading interface 106 or the frame 108. Similarly, in some embodiments, connection of the second side 122 of the sensor 114 to the loading interface or the frame is achieved by connecting the second side 122 of the sensor 114 to one or more components in the exercise apparatus that extend from the loading interface or the frame. For example, FIGS. 3-5 illustrate the connection through one or more bars or plates (e.g., 308, 408, 508) in the exercise apparatus that extend from the loading interface or the frame.

Referring to FIG. 7, in some embodiments, the linear adjustment system is a crank-driven mechanical system 702. Similar to the linear actuator 502, the crank-driven mechanical system 702 includes a fixed portion 704 and an extendable portion 706 axially aligned with the fixed portion 704. The extendable portion 706 is moveable with respect to the fixed portion 704 in the longitudinal direction of the crank-driven mechanical system 702. In one embodiment, the fixed portion 704 is hollow and the extendable portion is slidably disposed in the fixed portion.

The driven mechanical system 702 further includes a locking mechanism 708 to lock the extendable portion 706 at a selected position with respect to the fixed portion 704. In some embodiments, the locking mechanism 708 includes a handle, a knob, a dial or the like 710 for manually moving the extendable portion 706 with respect to the fixed portion 704 along the longitudinal direction of the linear adjustment system, thereby adjusting the length of the crank-driven mechanical system 702.

Referring to FIG. 8, in some embodiments, the linear adjustment system is a manually adjustable pin system 850. Similar to the linear actuator 502 and the crank-driven mechanical system 702, the manually adjustable pin system 850 includes a fixed portion 852 and an extendable portion 856 axially aligned with the fixed portion. The extendable portion 856 is moveable with respect to the fixed portion 852 in the longitudinal direction of the manually adjustable pin system 850. In one embodiment, the fixed portion 852 is hollow and the extendable portion 856 is slidably disposed in the fixed portion 852.

In some embodiments, the manually adjustable pin system 850 further includes a locking mechanism to lock the extendable portion 856 at a selected position with respect to the fixed portion 852. The locking mechanism includes a hole 860 formed on a wall of the fixed portion 856, and a plurality of holes 862 formed on a wall of the extending portion 856 and spaced apart from each other in the longitudinal direction of the linear adjustment system. The locking mechanism further includes a fastener 864 configured to engage the hole 860 on the fixed portion 852 with any one of the plurality of holes 862 on the extendable portion 856 to lock the extendable portion 856 with respect to the fixed portion 852.

By way of illustrations, FIG. 8 shows one substantially circular hole formed on the fixed portion and seven substantially circular holes on the extendable portion. It will be appreciated that configuration of the holes (e.g., size, shape, number of holes and locations of the holes on the fixed portion or the extendable portion) on the fixed portion and the extendable portion can be readily varied. For example, the holes on the fixed portion and on the extendable portion can have circular, oval, square, polygonal, elongated, or any suitable shapes in various sizes. As another example, the fixed portion can be formed with more than one hole.

In some embodiments, the length of the linear adjustment system (e.g., linear actuator 502, crank-driven mechanical system 602, or manually adjustable pin system 702) has a length extendable from 5 cm to 1200 cm, 10 cm to 1000 cm, or 30 cm to 500 cm. It will be appreciated that this range will depend upon the characteristics of the exercise machine.

In some embodiments, the linear adjustment system (e.g., linear actuator 502, crank-driven mechanical system 702, or manually adjustable pin system 850) is configured such that the length of the linear adjustment system and thence the length of the device 102 is adjustable continuously. In some embodiments, the linear adjustment system is configured such that the length of the linear adjustment system and thence the length of the device is incrementally adjustable by an increment amount. In some embodiments, the increment amount is a fixed amount that is between 0.3 inches and 0.5 inches, between 0.5 inches and 1.0 inch, between 1.0 inches and 1.5 inches, between 1.5 inches and 2.0 inches, between 2.0 inches and 2.5 inches, between 2.5 inches and 3.0 inches, between 3.0 inches and 3.5 inches, between 3.5 inches and 4.0 inches, between 4.0 inches and 4.5 inches, or between 4.5 inches and 5.0 inches, or SI equivalents thereof. In some embodiments, the increment amount is a fixed amount that is between 1 centimeter and 2 centimeters, between 2 centimeters and 3 centimeters, between 3 centimeters and 4 centimeters, between 4 centimeters and 5 centimeters, between 5 centimeters and 6 centimeters, between 6 centimeters and 7 centimeters, between 7 centimeters and 8 centimeters, between 8 centimeters and 9 centimeters, between 9 centimeters and 10 centimeters, or between 10 centimeters and 11 centimeters.

Figure 9:
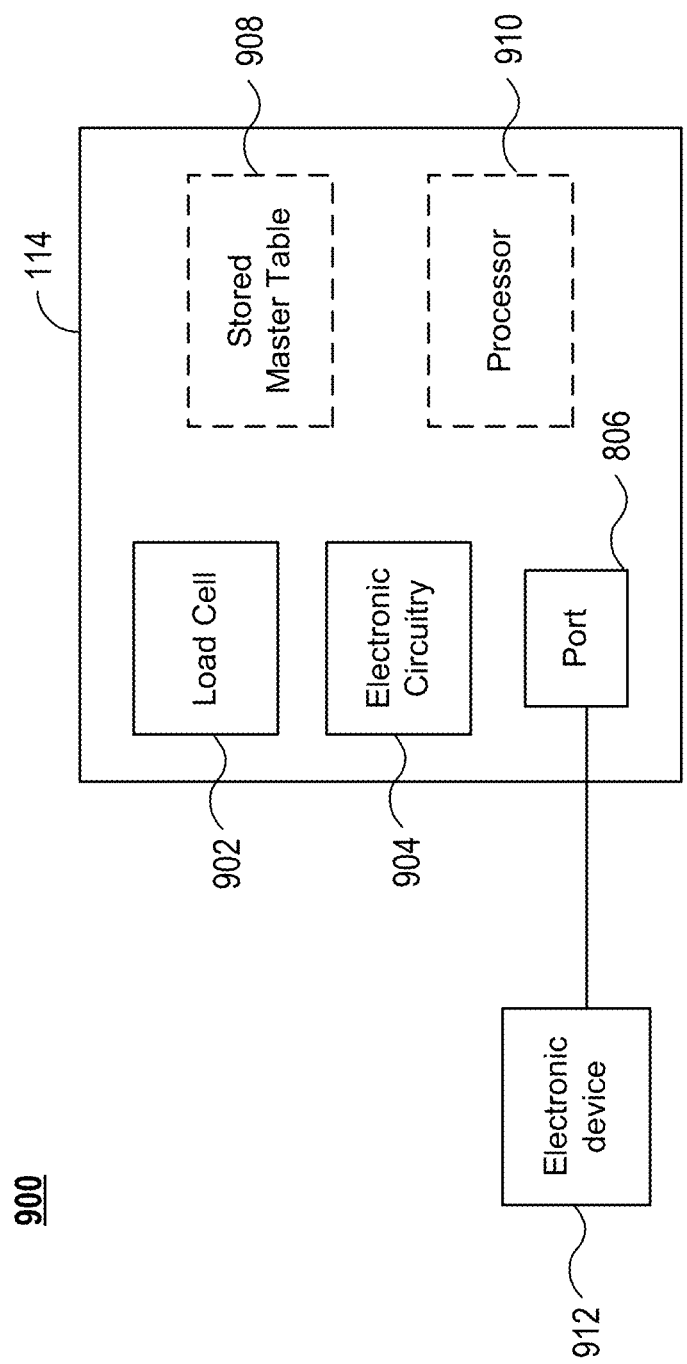
FIG. 9 is a schematic diagram illustrating a sensor of a device in accordance with an embodiment of the present disclosure.

Turning now to FIG. 9, there depicts a schematic diagram illustrating a sensor 114 of the device 102 in accordance with some embodiments of the present disclosure. As shown, in some embodiments, the sensor 114 includes a load cell 902 that outputs an analog signal in accordance with the force exerted on the linear adjustment system. In an embodiment, the load cell 902 includes a strain gauge load cell. In some embodiments, the sensor 114 also includes electronic circuitry 904 that converts the analog signal to a digital signal. In some embodiments, the sensor 114 further includes a port that outputs the digital signal. In some embodiments, the electronic circuitry converts the analog signal to a USB-compatible digital signal, and the port is a USB port.

In some embodiments, the correlation mechanism includes a master table to correlate the measured force on the linear adjustment system to an actual force exerted on the loading interface from the exercise. The master table is predetermined for the exercise apparatus or for various exercise apparatuses. In some embodiments, the master table such as the master table 908 is stored or embedded in the sensor 114 as illustrated in FIG. 9. In some embodiments, the predetermined master table 908 includes a set of forces measured by the sensor 114 and corresponding forces exerted on the loading interface for each functional position in the plurality of functional positions and for each weight in a plurality of weights.

In some embodiments, in the predetermined master table 908, the plurality of functional positions of the loading interface corresponds to the length of the device or the length of the linear adjustment system with a fixed increment amount that is between 0.3 inches and 0.5 inches, between 0.5 inches and 1.0 inch, between 1.0 inches and 1.5 inches, between 1.5 inches and 2.0 inches, between 2.0 inches and 2.5 inches, between 2.5 inches and 3.0 inches, between 3.0 inches and 3.5 inches, between 3.5 inches and 4.0 inches, between 4.0 inches and 4.5 inches, or between 4.5 inches and 5.0 inches.

In some embodiments, in the predetermined master table 908, a weight increment in the plurality of weights is varied. In some embodiments, in the predetermined master table 908, a weight increment in the plurality of weights is a fixed amount that is between 1 pound and 5 pounds, between 5 pounds and 10 pounds, between 10 pounds and 20 pounds, between 20 pounds and 30 pounds, between 30 pounds and 40 pounds, or between 40 pounds and 50 pounds. In some embodiments, in the predetermined master table 908, a weight increment in the plurality of weights is a fixed amount that is between 1 kilogram and 5 kilograms, between 5 kilograms and 10 kilograms, between 10 kilograms and 20 kilograms, between 20 kilograms and 30 kilograms, between 30 kilograms and 40 kilograms, or kilograms 40 pounds and 50 kilograms.

In some embodiments, the sensor 114 further includes a processor 910 that uses the predetermined master table 908 to determine the force exerted on the loading interface based on the force exerted on the linear adjustment system by an exerciser and the functional position of the loading interface.

Figure 1E:
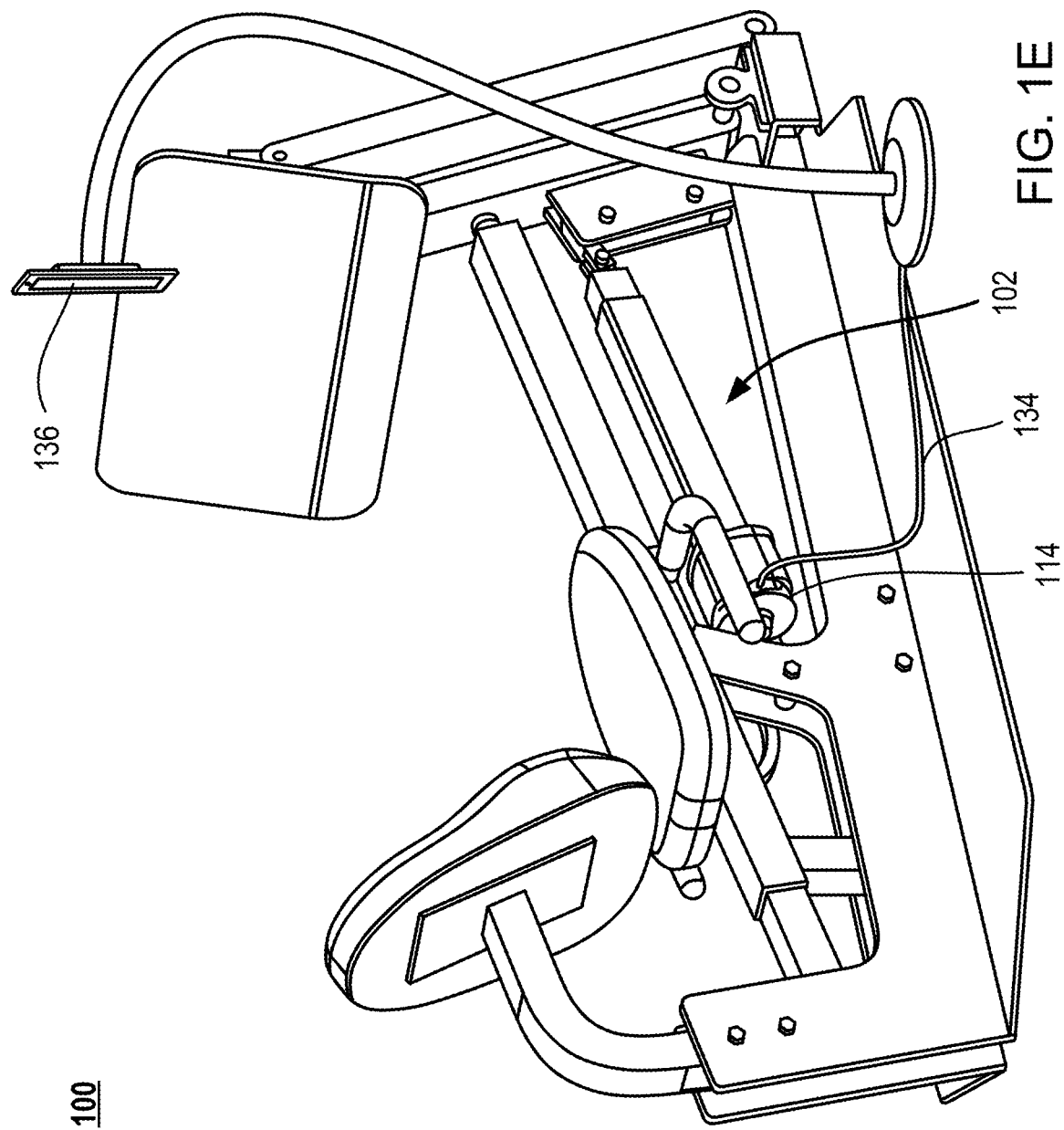
FIG. 1E is a back-right-hand-side perspective view of FIG. 1A.
Figure 1F:
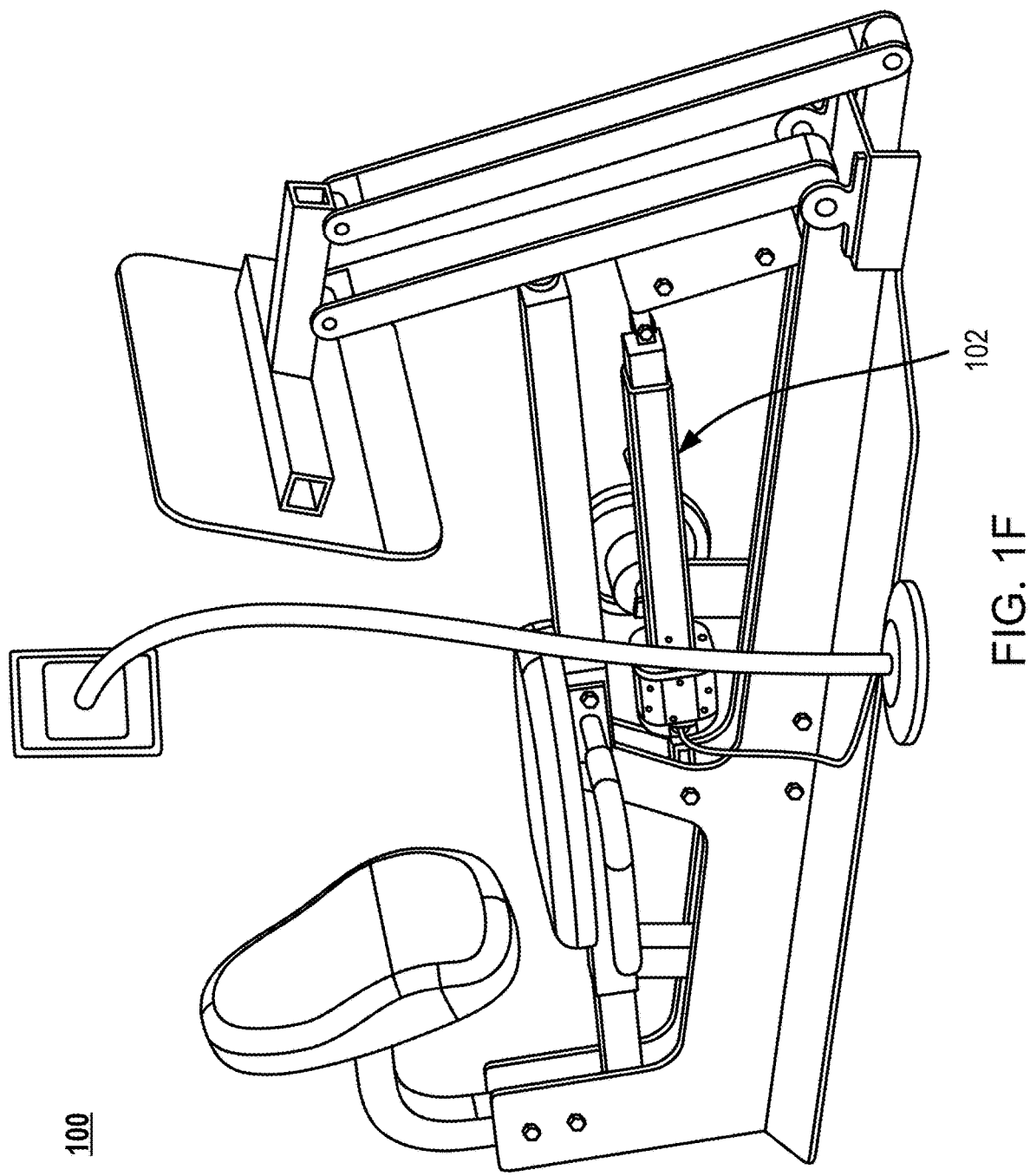
FIG. 1F is a front-right-hand-side perspective view of FIG. 1A.
Figure 1G:
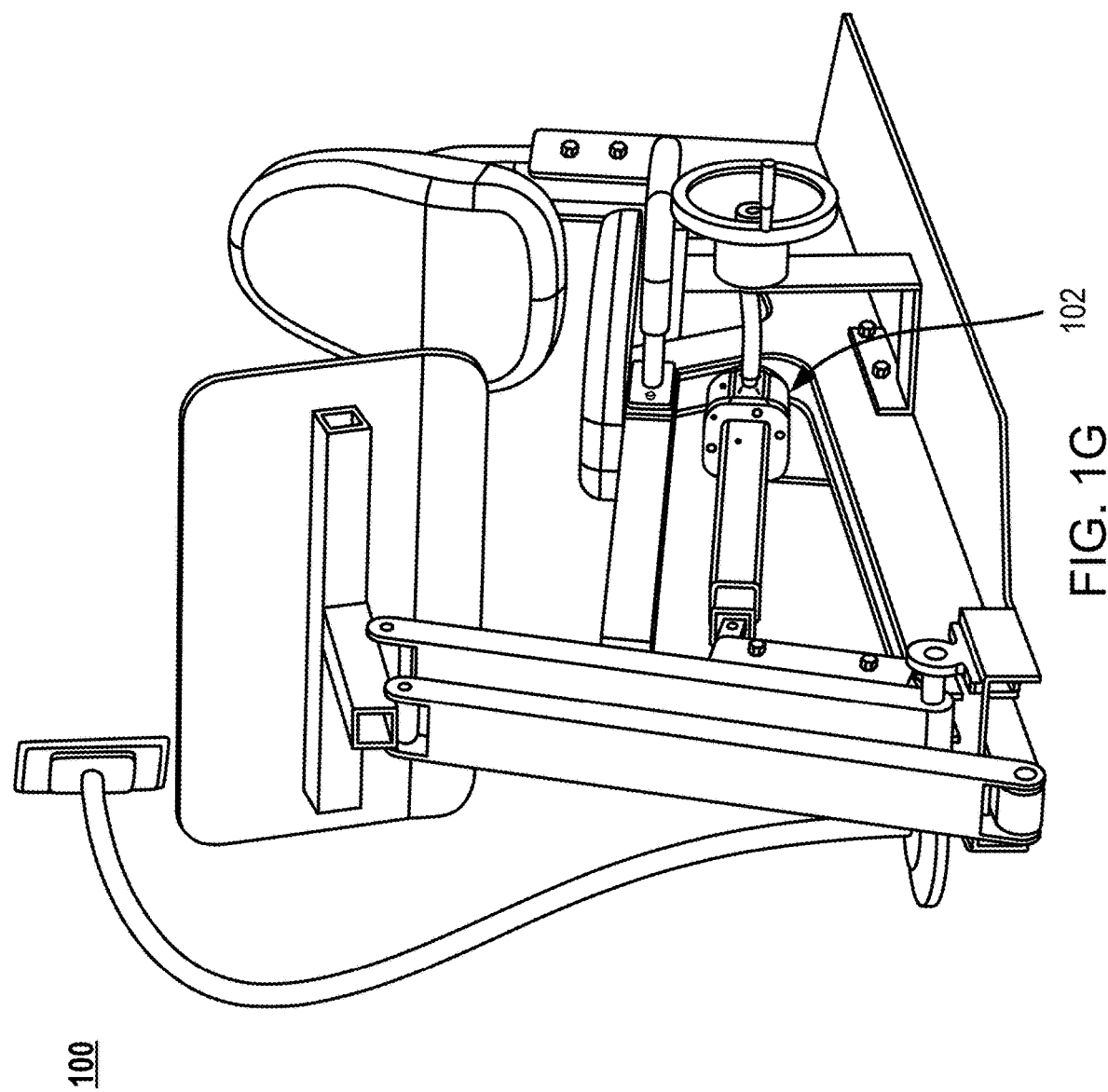
FIG. 1G is a front-left-hand-side perspective view of FIG. 1A.
Figure 1H:
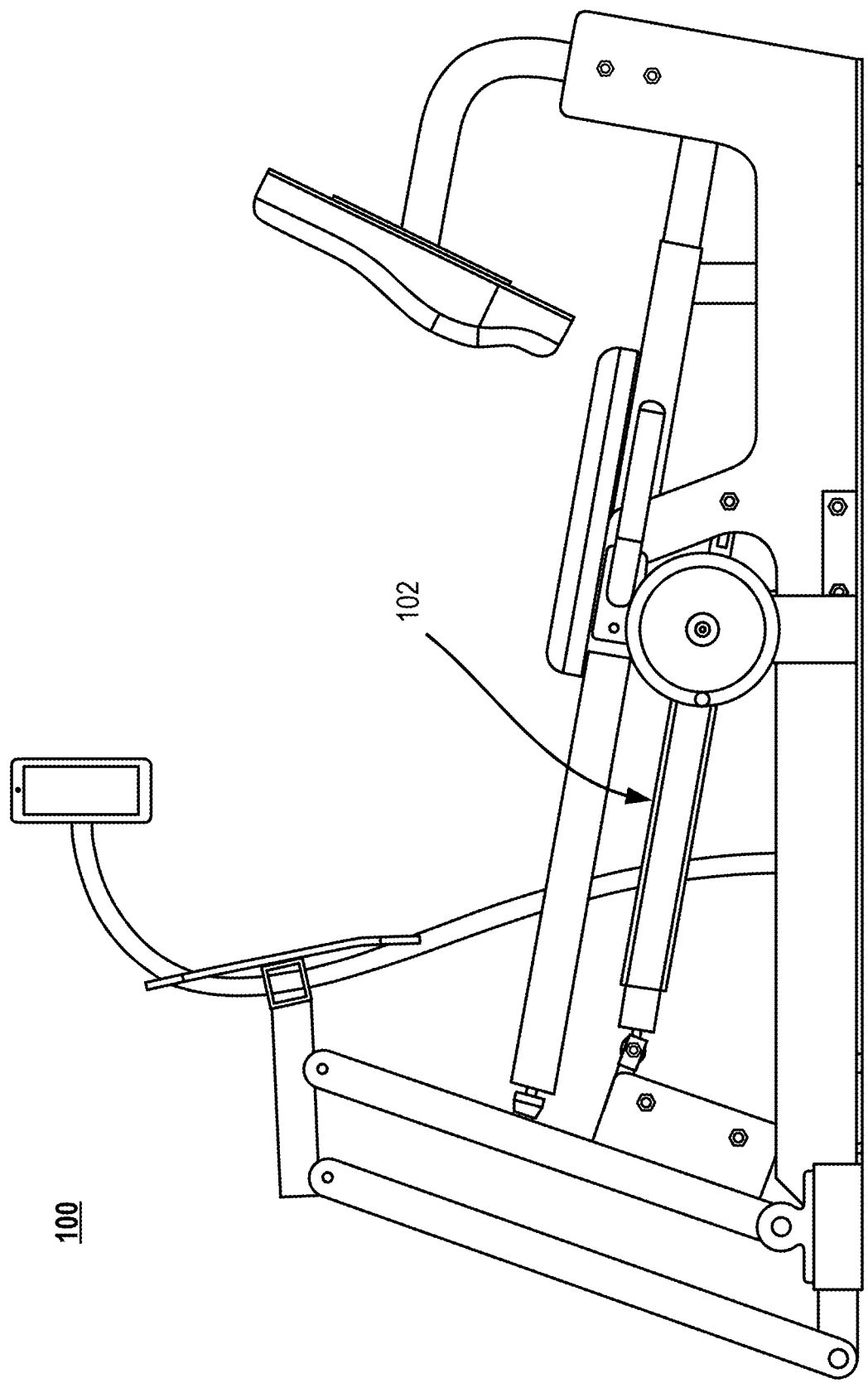
FIG. 1H is a left-hand-side view of FIG. 1A.
Figure 1I:
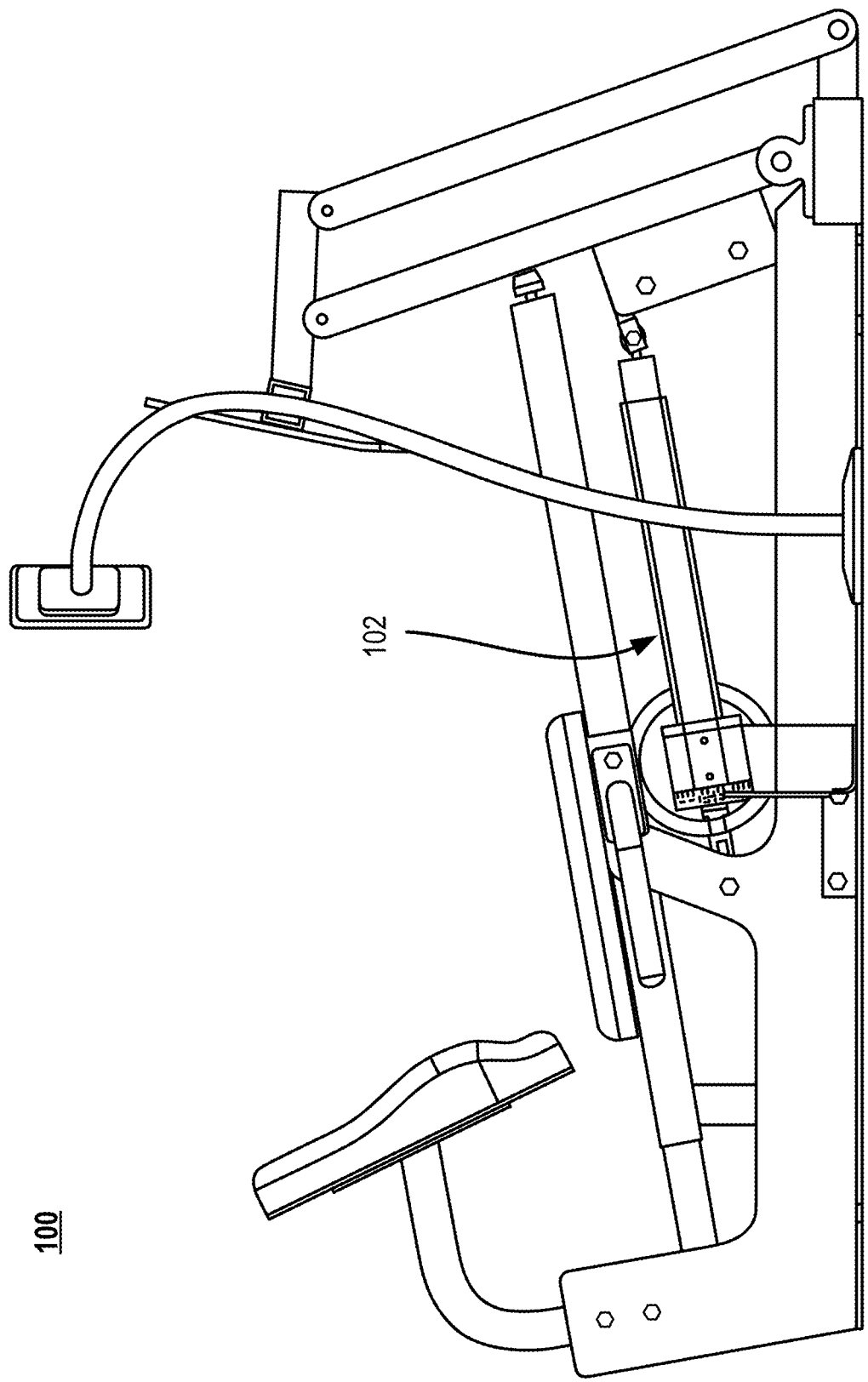
FIG. 1I is a right-hand-side view of FIG. 1A.
Figure 1J:
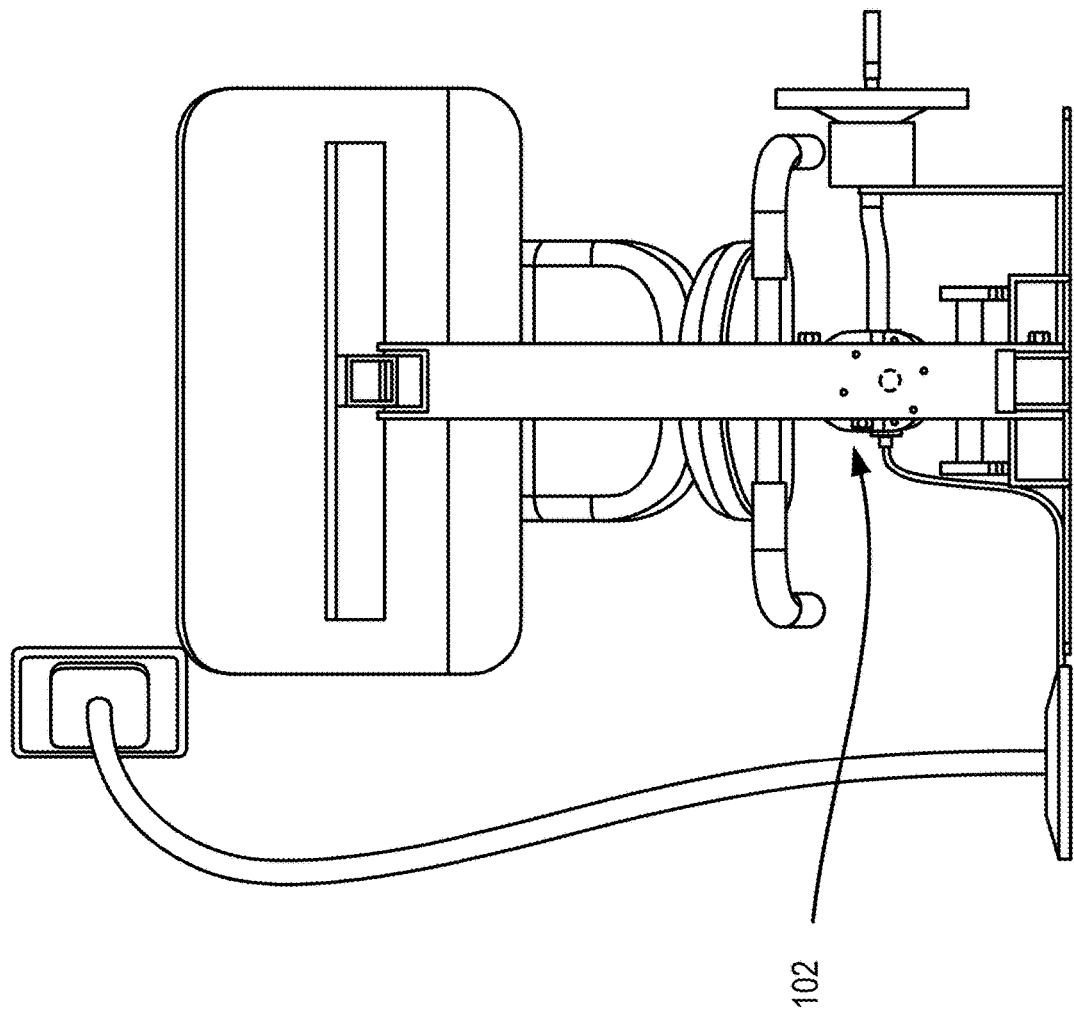
FIG. 1J is a front view of FIG. 1A.
Figure 1K:
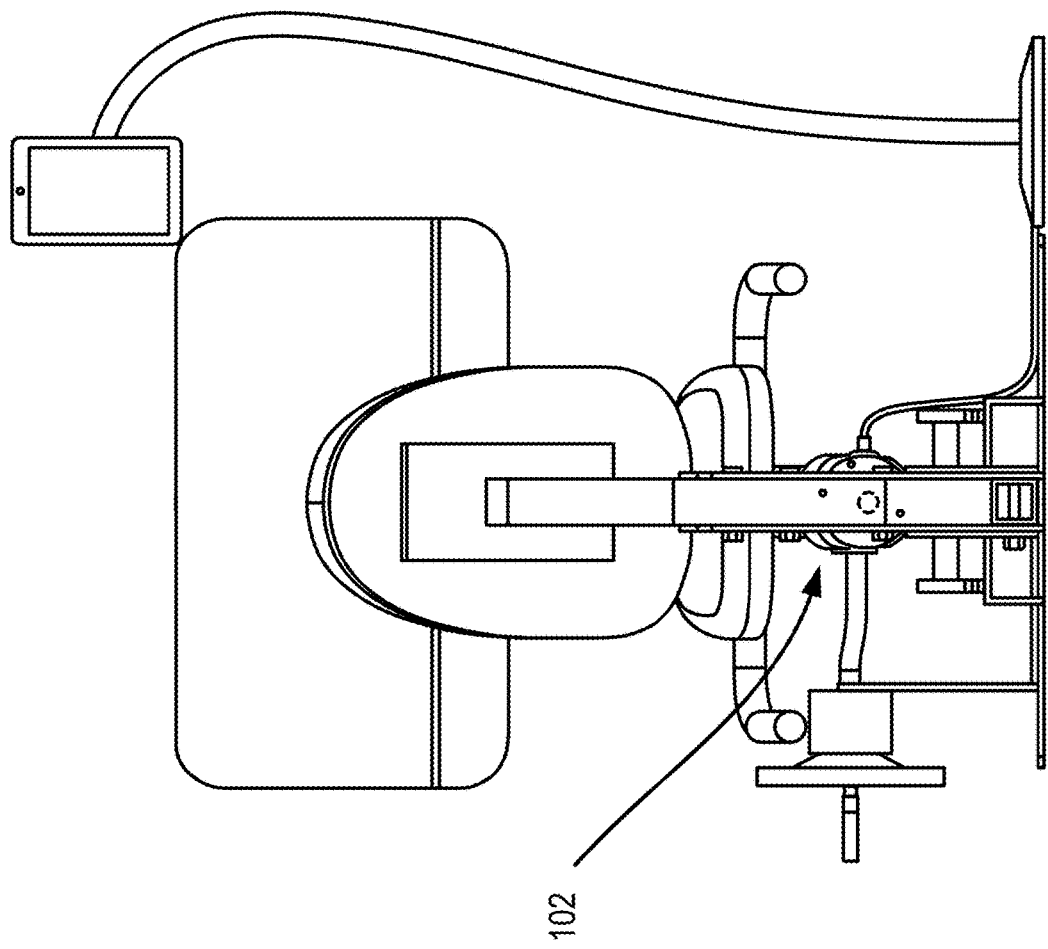
FIG. 1K is a back view of FIG. 1A.
Figure 1L:
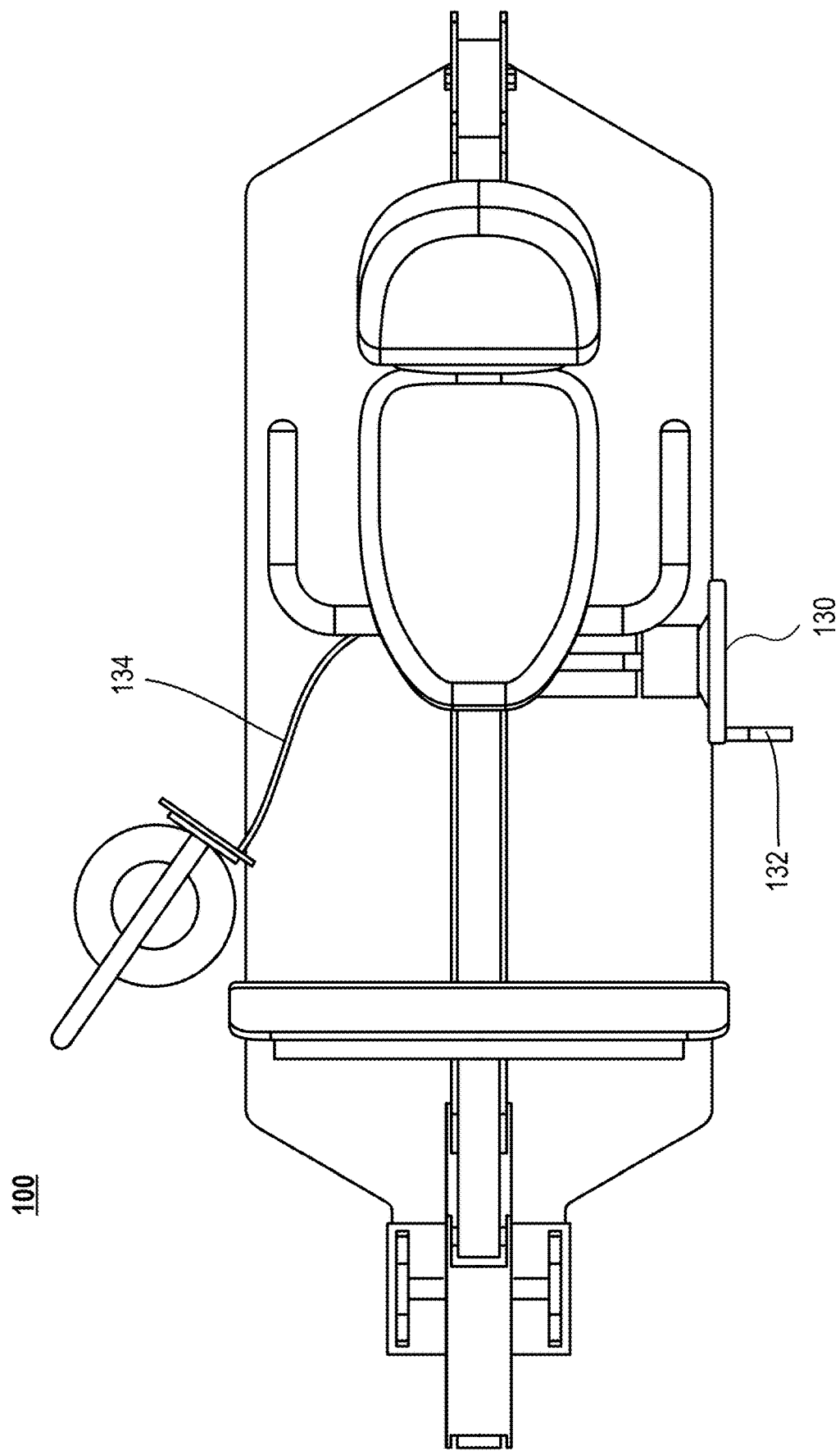
FIG. 1L is a top view of FIG. 1A.
Figure 1M:
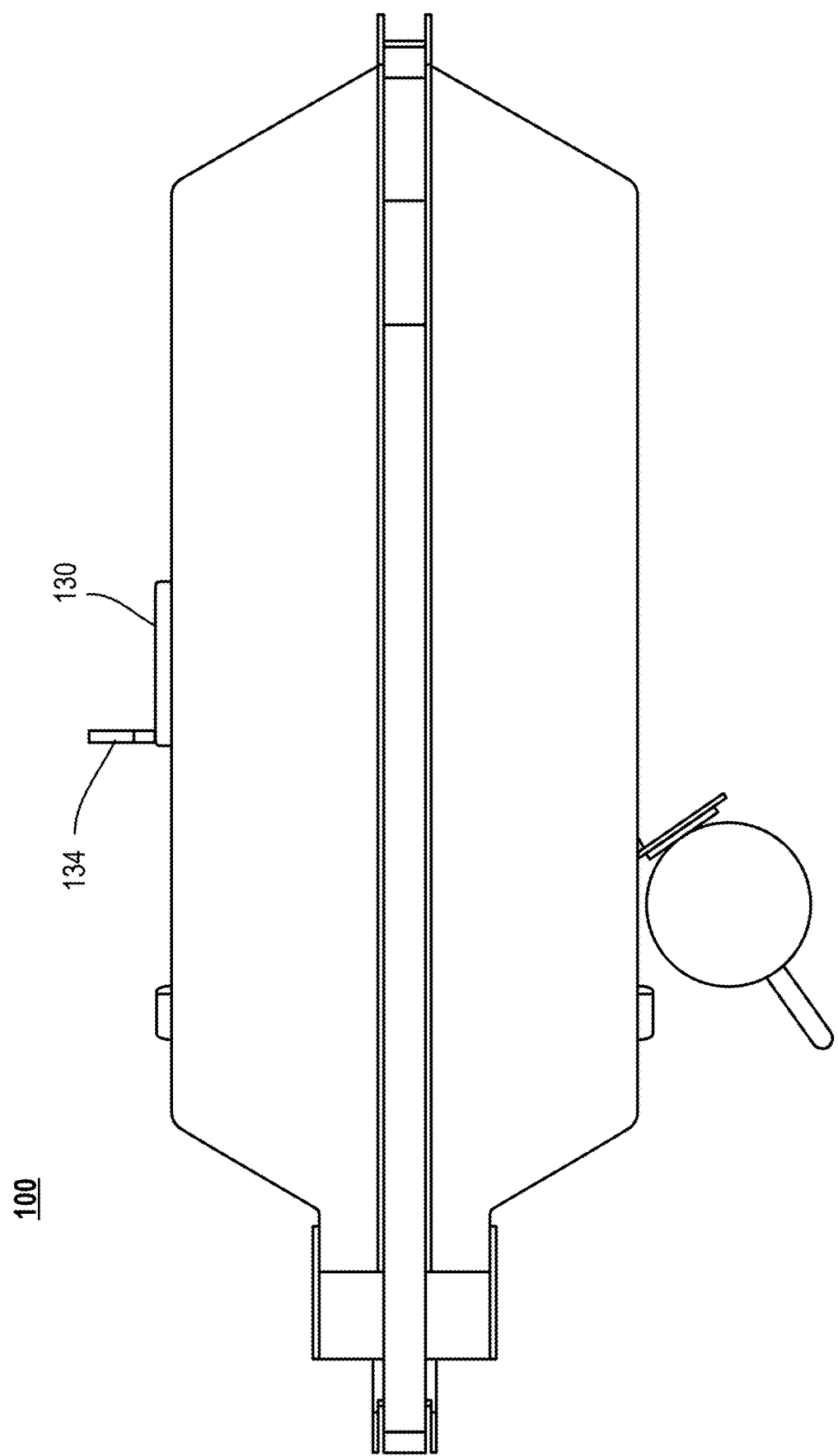
FIG. 1M is a bottom view of FIG. 1A.

In some embodiments, the sensor 114 is electrically or wirelessly connected to an electronic device 912. The sensor 114 outputs the measured force on the linear adjustment system, the force exerted on the loading interface of the exercise apparatus or both forces to the electronic device 912. In some embodiments, the electronic device 912 is a display, a smartphone, a computer, a server, a receiver, or other electronic devices and systems. By way of illustration, FIG. 1E illustrates the sensor 114 connected to an electronic device 136 (e.g., display, monitor, or screen) via a cable 134. In some embodiments, the electronic device performs one or more of the following: (i) displaying the measured force on the linear adjustment system, the force exerted on the loading interface or both forces, and (ii) determining an osteogenic loading based on the one or more of the measured force on the linear adjustment system and the force exerted on the loading interface. The term "osteogenic loading" used herein refers to optimal functional positions and highest possible loads applied at optimal functional positions.

Figure 10:
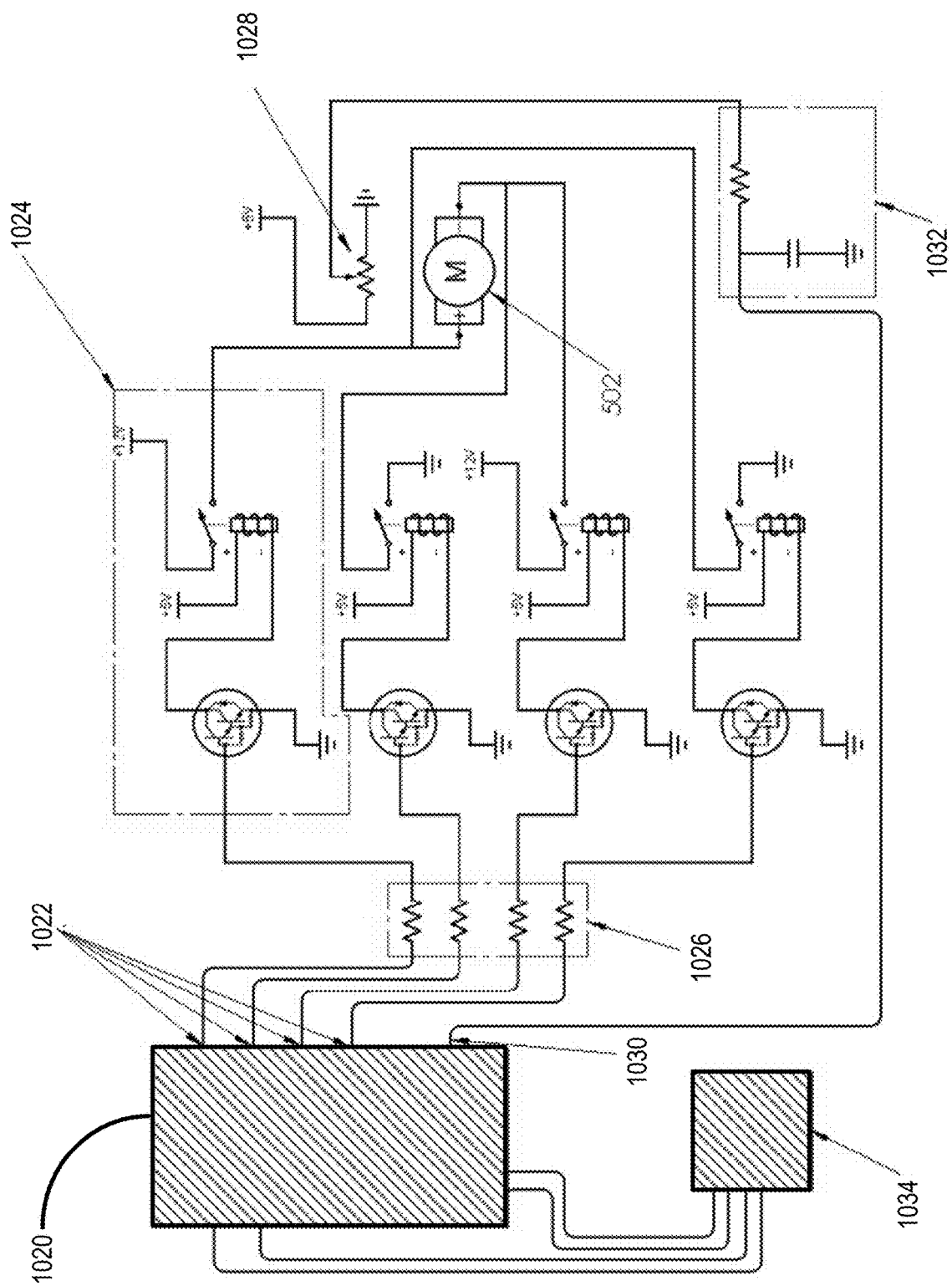
FIG. 10 is a schematic diagram illustrating an embedded electrical system in accordance with an embodiment of the present disclosure.

In some embodiments in which the linear adjustment mechanism is electrically controlled, such as embodiments where the linear adjustment system is a linear actuator, the claimed invention includes a system such as that in FIG. 10 which provides for the control of an actuator 502 as illustrated in FIGS. 2A, 2B, 3, 4, and 5. In some embodiments that control system includes a microcontroller, processor, System On a Chip, or computer 1020 that directly regulates current flow using analog or digital output pins 1022 to activate or deactivate one or more electrically controlled power switching mechanisms 1024, which consist of electromechanical relays, solid state relays, MOSFETS, H-Bridge MOSFETS, Power Transistors, Darlington Transistors, thyristors or any combination of the preceding or similar devices. In some embodiments the signal outputs 1022 used to modulate the power switching components 1024 exhibit current limiting resistors 1026 to protect the digital or analog outputs of the processor 1020 from excessive current draw.

In some embodiments of the present disclosure where the linear adjustment mechanism is a linear actuator 502, that actuator has a potentiometer 1028 integrated into it so as to provide an analog signal indicating the degree of its extension. In some embodiments the processor 1020 accepts the analog input 1030 from the potentiometer to permit proper adjustment and display of the actuator's 502 position. Some embodiments incorporate hardware filtering of this signal, such as by a first order low pass filter 1032, or any similarly functional hardware signal conditioning technique.

In some embodiments the processor 1020 is an embedded computer or sophisticated microcontroller capable of managing actuator movement, reading load cell output, displaying the required data to a screen, and accepting commands from the user via a touch screen, hardware buttons, or otherwise.

In some embodiments the processor 1020 is a low power microcontroller that operates as a slave or peripheral device to a master electronic device such as 812 illustrated in FIG. 2B. In some embodiments the processor 1020 illustrated in FIG. 10 is connected by a cable to the master device. In other embodiments the processor 1020 is connected to or incorporates a wireless transceiver 1034, which uses Bluetooth, RF, WiFi, or a similar wireless protocol to communicate with the master device. In some embodiments the master device is a component of the exercise machine, and in some embodiments it may be a multipurpose electronic device such as a tablet, smartphone, or laptop which belongs to the user and is only temporarily paired with and used to control the processor 1020. In some embodiments the processor 1020 controls the actuator and accepts a digital or analog signal generated by a force sensor. In some embodiments the processor 1020 amplifies, filters, or translates the signal from the force sensor and provides it to the master electronic device.

In some embodiments the entirety of the circuitry, other than the actuator 502 and its potentiometer 1028, described in FIG. 10, is stored in the embedded electronics enclosure 516 shown in FIG. 2B.

REFERENCES CITED AND ALTERNATIVE EMBODIMENTS

All references cited herein are incorporated herein by reference in their entirety and for all purposes to the same extent as if each individual publication or patent or patent application was specifically and individually indicated to be incorporated by reference in its entirety for all purposes.

The present invention can be implemented as a computer program product that comprises a computer program mechanism embedded in a nontransitory computer readable storage medium. For instance, the computer program product could contain the program modules shown in FIG. 2D. These program modules can be stored on a CD-ROM, DVD, magnetic disk storage product, or any other non-transitory computer readable data or program storage product.

Many modifications and variations of this invention can be made without departing from its spirit and scope, as will be apparent to those skilled in the art. The specific embodiments described herein are offered by way of example only. The embodiments were chosen and described in order to best explain the principles of the invention and its practical applications, to thereby enable others skilled in the art to best utilize the invention and various embodiments with various modifications as are suited to the particular use contemplated. The invention is to be limited only by the terms of the appended claims, along with the full scope of equivalents to which such claims are entitled.

What is claimed:

1. An exercise apparatus, wherein the exercise apparatus comprises a loading interface and a frame coupled to the loading interface for performing an exercise, the exercise apparatus comprising:
   a linear adjustment system that is configured to adjust an initial position of the loading interface at any one of a plurality of functional positions in a functional range of the loading interface, wherein the functional range comprises a first terminal functional position, one or more intermediate positions, and a second terminal functional position, wherein,
   the linear adjustment system comprises a first end and a second end, and
   the first end is configured to be fixedly connected to one of the loading interface and the frame; and
   wherein,
   the exercise exerts a muscle group of a subject through a range of motion, the range of motion comprises a first subrange that is characterized by a first maximum force that can be exerted by the subject,
   the range of motion further comprises a second subrange that is characterized by a second maximum force that can be exerted by the subject,
   the second maximum force is greater than the first maximum force,
   the initial position of the loading interface is a position in the functional range of the loading interface that permits the subject to exert a force on the loading interface with the muscle group at a point in the range of motion that is in the second subrange without any requirement of passing through the first subrange, and
   the loading interface is further from the first terminal functional position throughout the entire second subrange than it is throughout the entire first subrange.

2. The exercise apparatus of claim 1, wherein the exercise apparatus is a leg press apparatus, an adjustable cable apparatus, a chest press apparatus, bench press apparatus, a vertical lift apparatus, a core apparatus, or a combination thereof.

3. The exercise apparatus of claim 1, further comprising a sensor comprising a first side fixedly coupled to the second end of the linear adjustment system and a second side fixedly coupled to the other of the loading interface and the frame, wherein the sensor measures a force exerted on the linear adjustment system, and the sensor outputs a signal in accordance with the force exerted on the loading interface.

4. The exercise apparatus of claim 3, wherein the sensor comprises:
   a load cell that outputs an analog signal in accordance with the force exerted on the linear adjustment system;
   electronic circuitry for converting the analog signal to a digital signal; and
   a port that outputs the digital signal.

5. The exercise apparatus of claim 3, wherein:
   the sensor stores a predetermined master table for the exercise apparatus, and
   for each functional position in the plurality of functional positions and for each weight in a plurality of weights, the predetermined master table includes a set of forces measured by the sensor and corresponding forces exerted on the loading interface.

6. The exercise apparatus of claim 3, further comprising a first connector fixedly connecting the first end of the linear adjustment system with one of the loading interface and the frame, and a second connector fixedly connecting the second side of the sensor with the other of the loading interface and the frame.

7. The exercise apparatus of claim 6, further comprising a third connector fixedly connecting the second end of the linear adjustment system with the first side of the sensor.

8. The exercise apparatus of claim 3, wherein:
   the first end is directly fixedly connected to one of the loading interface and the frame of the exercise apparatus, and
   the second side of the sensor is directly fixedly connected with the other of the loading interface and the frame of the exercise apparatus.

9. The exercise apparatus of claim 3, wherein the sensor is electrically or wirelessly connected to a monitor device, and the sensor outputs to the monitor device a measured force on the linear adjustment system or the force exerted on the loading interface of the exercise apparatus.

10. The exercise apparatus of claim 9, wherein the monitor device is a display, a smartphone, a computer, a server, or a receiver.

11. The exercise apparatus of claim 9, wherein the monitor device provides a numerical or graphical comparison of a current force output in a current session by the subject with the exercise apparatus that is fixed by the linear adjustment system to any one of:
   (i) a magnitude of a force generated by the subject in a session with the exercise apparatus immediately prior to the current session with the exercise apparatus by the subject,
   (ii) in a prior session with the exercise apparatus for which a highest force was achieved by the subject, and
   (iii) a first ever session the subject had with the exercise apparatus.

12. The exercise apparatus of claim 1, further comprising a peripheral device comprising a power switching circuit or a servo motor controller that adjusts the position of the loading interface based on one or more instructions provided to a controller coupled to the linear adjustment system and the peripheral device.

13. The exercise apparatus of claim 12, wherein the subject manually adjusts the position of the loading interface by providing the one or more instructions through the controller of the exercise apparatus.

14. The exercise apparatus of claim 1, wherein the subject manually adjusts the position of the loading interface.

15. The exercise apparatus of claim 1, wherein a respective distance between each position in the one or more intermediate positions is uniform.

16. The exercise apparatus of claim 15, wherein the respective uniform distance is in a range of from 0.7 centimeters (cm) to 12.7 cm.

17. The exercise apparatus of claim 1, wherein the linear adjustment system is configured so that a length of the linear adjustment system is incrementally adjustable by a linear increment amount through a plurality of linear increment positions, wherein each linear increment position in the plurality of linear increment positions uniquely corresponds to a functional position in the plurality of functional positions of the loading interface.

18. The exercise apparatus of claim 1, wherein the loading interface is configured to extend, retract, or pivot between each functional position in the plurality of functional positions.

19. The exercise apparatus of claim 1, wherein the linear adjustment system comprises:
   a fixed portion, an extendable portion axially aligned with the fixed portion, wherein the extendable portion is moveable with respect to the fixed portion in a linear direction, and a locking mechanism to lock the extendable portion at a selected position with respect to the fixed portion.

20. The exercise apparatus of claim 19, wherein the fixed portion and the extendable portion are concentric.

* * * * *